US007674465B1

(12) United States Patent
Rest et al.

(10) Patent No.: US 7,674,465 B1
(45) Date of Patent: Mar. 9, 2010

(54) REGULATION OF GENE EXPRESSION BY THE *BACILLUS ANTHRACIS* ARP

(75) Inventors: Richard F. Rest, Rosemont, PA (US); Daniel J. Simon, Wayne, PA (US); Elise M. Mosser, Exton, PA (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 11/767,815

(22) Filed: Jun. 25, 2007

Related U.S. Application Data

(60) Provisional application No. 60/816,017, filed on Jun. 23, 2006, provisional application No. 60/857,862, filed on Nov. 10, 2006.

(51) Int. Cl.
*A61K 39/00* (2006.01)
*A61K 39/02* (2006.01)
*A61K 39/04* (2006.01)

(52) U.S. Cl. .................. 424/185.1; 424/9.1; 424/9.2; 424/243.1; 530/300; 530/350; 536/23.1; 536/23.7

(58) Field of Classification Search .................. 424/9.1, 424/9.2, 185.1, 243.1; 530/300, 350; 536/23.1, 536/23.7
See application file for complete search history.

(56) References Cited

U.S. PATENT DOCUMENTS

| 5,530,195 | A | 6/1996 | Kramer et al. |
| 6,218,122 | B1 | 4/2001 | Friend et al. |
| 6,329,156 | B1 | 12/2001 | Cirino et al. |
| 6,387,665 | B1 | 5/2002 | Ivins et al. |
| 2006/0089305 | A1 | 4/2006 | Rest et al. |

OTHER PUBLICATIONS

Mosser EM, Rest RF. The *Bacillus anthracis* cholesterol-dependent cytolysin, Anthrolysin O, kills human neutrophils, monocytes and macrophages. BMC Microbiol. Jun. 21, 2006;6:56.
Ross CL, Koehler TM. plcR papR-independent expression of anthrolysin O by *Bacillus anthracis*.J Bacteriol. Nov. 2006;188(22):7823-9.
Park JM, Ng VH, Maeda S, Rest RF, Karin M. Anthrolysin O and other gram-positive cytolysins are toll-like receptor 4 agonists. J Exp Med. Dec. 20, 2004;200(12):1647-55.
Shannon JG, Ross CL, Koehler TM, Rest RF. Characterization of anthrolysin O, the *Bacillus anthracis* cholesterol-dependent cytolysin. Infect Innmun. Jun. 2003;71(6):3183-9.

*Primary Examiner*—Rodney P. Swartz
(74) *Attorney, Agent, or Firm*—Caesar, Rivise, Bernstein, Cohen & Pokotilow, Ltd.

(57) ABSTRACT

The invention provides a novel gene and protein regulating the expression of *Bacillus anthracis* Anthrolysin O toxin, pharmaceutical compositions and antibodies which may be utilized for human or veterinary applications or for agricultural applications, and methods of treatment using same.

18 Claims, 13 Drawing Sheets

Figure 1

Figure 9

Figure 2:
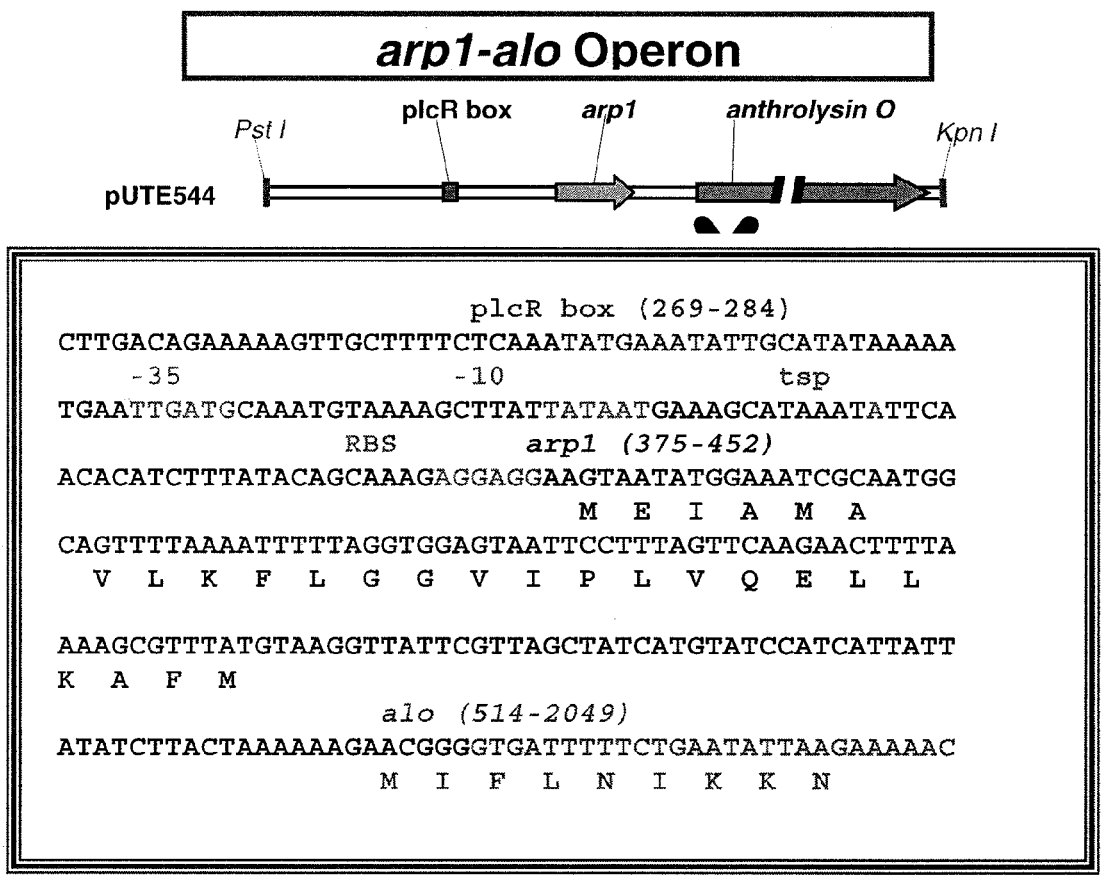

| Fold change (up/down) | p-value (Limma FDR) | No of genes (two step) |
|---|---|---|
| 2 | 0.01 | 1659 |
| 2 | 0.05 | 2097 |
| 3 | 0.01 | 426 |
| 3 | 0.05 | 532 |
| 4 | 0.01 | 112 |
| 4 | 0.05 | 144 |
| 5 | 0.01 | 44 |
| 5 | 0.05 | 54 |

Figure 10

| Nfold | Gene | Description, Comments |
|---|---|---|
| 2.86 | | uroporphyrinogen-III synthetases |
| 2.54 | | uroporphyrinogen decarboxylase |
| 3.52 | | molybdenum ABC transporter, permease protein |
| 2.57 | | molybdate-binding protein (carboxy terminus) |
| 2.99 | nirC? | formate nitrite transporter family protein |
| 3.07 | hmp | flavohemoprotein; homolog of flavohemoglobin |
| 1.74 | resA | thiol-disulfide oxidoreductase; cytochrome $c$ maturation |
| 1.39 | resB | resB protein; cytochrome $c$ synthesis |
| 2.03 | resC | resC protein; cytochrome $c$ synthesis |
| 1.91 | resD | DNA-binding response regulator; aerobic/anaerobic respiration |
| 1.44 | resE | sensor histidine kinase; aerobic/anaerobic respiration |
| 3.43 | narG | respiratory nitrate reductase, alpha subunit; bis-MGD (bis-molybdenum guanine dinucleotide) containing catalytic site |
| 3.99 | narH | respiratory nitrate reductase, beta subunit; electron transfer component binding 4 iron–sulphur clusters |
| 5.01 | narJ | nitrate reductase, delta chain; chaperone function |
| 6.80 | narI | respiratory nitrate reductase, gamma subunit; the di-$b$-haem integral membrane NarI quinol dehydrogenase subunit anchors the nitrate reductase complex to the membrane |
| 2.82 | crp, fnr | transcriptional regulator, Crp Fnr family; regulator of anaerobically induced genes |
| 4.54 | nar-A1 | molybdenum cofactor biosynthesis protein A; moaA homolog |
| 2.58 | | molybdenum cofactor biosynthesis protein A, N-terminus |
| 2.56 | | molybdenum cofactor biosynthesis protein A, C-terminus |
| 2.62 | Moe-B | molybdopterin biosynthesis protein MoeB; . ATP-dependent adenylate transferase, modifies MoeD of molybdopterin |
| 2.89 | Moe-A1 | molybdopterin biosynthesis protein |
| 2.96 | Moa-D1 | molybdopterin converting factor, subunit 2 |
| 3.69 | Moa-E1 | molybdopterin converting factor, subunit 1 |
| 5.75 | narK | Nitrate/nitrite transporter; nitrate/proton symport and nitrate/nitrite antiport; transmembrane transporter superfamily |
| 3.91 | nasF | precorrin-2 dehydrogenase; catalyzes the formation of sideroheme from precorrin-2 |
| 2.87 | nasE | uroporphyrin-III C-methyltransferase; biosynthesis of precorrin-2 and precorrin-1 |
| 2.94 | nasD | nitrite reductase |
| 2.25 | | molybdenum cofactor biosynthesis protein A |
| 3.47 | MoaC | molybdenum cofactor biosynthesis protein C; molybdenum cofactor biosynthesis |
| 1.71 | | molybdenum cofactor biosynthesis protein B, putative |
| 2.56 | | molybdenum cofactor biosynthesis protein A, C-terminus |
| 2.58 | | molybdenum cofactor biosynthesis protein A, N-terminus |

Figure 11

| N-fold | p value (t test) | Gene description |
|---|---|---|
| 3.27 | 0.000102 | superoxide dismutase, Mn |
| 2.69 | 0.000156 | superoxide dismutase, Mn |
| 1.21 | 0.197721 | superoxide dismutase, Cu-Zn |
| 1.61 | 0.022813 | catalase |
| 1.32 | 0.074772 | catalase, Mn-containing |
| 3.18 | 0.000111 | germination protein gerN |
| 2.85 | 0.00493 | spore germination protein GerXC |
| 2.66 | 0.00139 | spore germination protein GerD |
| 2.36 | 0.007949 | spore germination protein GerXA |
| 2.08 | 0.008667 | spore germination protein GerXB |
| 1.84 | 0.014329 | spore germination protein GerAA |
| 1.69 | 0.005198 | germination protein GerE |
| 1.13 | 0.433545 | spore germination protein GerHB |
| 3.64 | 0.000228 | arginase |
| 2.46 | 0.000377 | immune inhibitor A metalloprotease |
| 1.54 | 0.000532 | alanine racemase |
| 1.51 | 0.050593 | alanine racemase |
| 3.77 | 3.48E-05 | 1-pyrroline-5-carboxylate dehydrogenase |

Figure 12

| N fold | P value (t test) | Gene description |
|---|---|---|
| 57.42 | 6.17E-05 | thiol-activated cytolysin (*alo*) |
| 32.98 | 3.69E-05 | intergenic region 3088531-3088936 (*arp1*) |
| 3.84 | 0.000143 | metallo-beta-lactamase family protein |
| 3.57 | 0.005657 | acetyltransferase, GNAT family |
| 3.46 | 1.7E-05 | tellurium resistance protein, putative |
| 2.77 | 0.049597 | ScdA protein |
| 2.72 | 3.55E-05 | tellurium resistance protein, putative |
| 2.61 | 5.26E-05 | tellurium resistance protein |
| 2.57 | 0.000491 | histidyl-tRNA synthetase |
| 2.42 | 1.33E-05 | rrf2 family protein |
| 1.8 | 0.00924 | transcriptional regulator, PlcR |
| 1.65 | 0.094882 | enterotoxin |
| 1.5 | 0.000555 | neutral protease |
| 1.23 | 0.012232 | channel protein, hemolysin III family |

Figure 13

| PHENOTYPE | OBSERVATION |
|---|---|
| Growth – BHI plate – anaerobic | colonies observable at 24 hours; none observed for BA663; BA558 grows much faster on plates under anaerobic conditions than does BA663. |
| Growth – BHI broth – aerobic | no phenotype; BA558 has the same growth rate in rich medium as BA663. |
| Hemolysis of human RBC – BHI overnight supernatants | !! no phenotype; BA558 expresses ALO in the absence of *arp1* !! |
| Hemolysis of human RBC – [BHI plus bicarbonate] O/N supernatants | no hemolysis: BA558 supernatants show absolutely no hemolysis; we believe this is due to the expression of proteases that cleave ALO, not to the lack of expression of ALO. *arp1* activity is affected by CO2 (bicarbonate). On the contrary, BA663 expressed *more* hemolysis in the presence of bicarbonate than in the absence. |
| ALO expression by Western analysis of [BHI plus bicoarbonate] O/N supernatants | ALO is expressed but cleaved, thus the lack of hemolysis. |
| sporulation | no phenotype; BA558 sporulates at the same rate as BA663 in sporulation medium |
| germination in 10% | germination is delayed >60 minutes; BA558 initiates germination or outgrowth more slowly than BA663 |
| germination with macrophages, in culture | germination is delayed >60 minutes; BA558 initiates germination or outgrowth more slowly than BA663 |
| sliver stained or Coomassie stained SDS-PAGE gels of whole bacteria grown O/N in BHI | A few major differences observed, especially two major proteins as 'ghosts' in silver gels, but stained with Coomassie. Need to do microarray analyses. |
| complementation with pDUM105, the *arp1* plasmid | BA558(pDUM105) makes ~100-fold more ALO than does BA558, as expected. |
| PA (*pag*) expression by Western analysis | no phenotype; BA558 expresses as much PA as BA663. |

SEQUENCE LISTING

<160> NUMBER OF SEQ ID NOS: 9

<210> SEQ ID NO 1
<211> LENGTH: 77
<212> TYPE: DNA
<213> ORGANISM: Bacillus anthracis

<400> SEQUENCE: 1
atggaaatcg caatggcagt tttaaaattt ttaggtggag taattccttt agttcaagaa    60
cttttaaaag cgtttat                                                   77

<210> SEQ ID NO 2
<211> LENGTH: 25
<212> TYPE: PRT
<213> ORGANISM: Bacillus anthracis

<400> SEQUENCE: 2

Met Glu Ile Ala Met Ala Val Leu Lys Phe Leu Gly Gly Val Ile Pro
1               5                   10                  15

Leu Val Gln Glu Leu Leu Lys Ala Phe
            20                  25

<210> SEQ ID NO 3
<211> LENGTH: 78
<212> TYPE: DNA
<213> ORGANISM: Bacillus anthracis

<400> SEQUENCE: 3
atggaaatcg caatggcagt tttaaaattt ttaggtggag taattccttt agttcaagaa    60
cttttaaaag cgtttatg                                                  78

<210> SEQ ID NO 4
<211> LENGTH: 26
<212> TYPE: PRT
<213> ORGANISM: Bacillus anthracis

<400> SEQUENCE: 4

Met Glu Ile Ala Met Ala Val Leu Lys Phe Leu Gly Gly Val Ile Pro
1               5                   10                  15

Leu Val Gln Glu Leu Leu Lys Ala Phe Met
            20                  25

<210> SEQ ID NO 5
<211> LENGTH: 16
<212> TYPE: DNA
<213> ORGANISM: Bacillus anthracis

<400> SEQUENCE: 5
tatgaaatat tgcata                                                    16

<210> SEQ ID NO 6
<211> LENGTH: 300
<212> TYPE: DNA
<213> ORGANISM: Bacillus anthracis

```
<400> SEQUENCE: 6
cttgacagaa aaagttgctt ttctcaaata tgaaatattg catataaaaa tgaattgatg      60
caaatgtaaa agcttattat aatgaaagca taaatattca acacatcttt atacagcaaa     120
gaggaggaag taatatggaa atcgcaatgg cagtttaaa attttaggt ggagtaattc       180 ctttagttca agaactttta aaagcgttta tgtaaggtta ttcgttagct atcatgtatc     240
catcattatt atatcttact aaaaaagaac ggggtgattt ttctgaatat taagaaaaac    300

<210> SEQ ID NO 7
<211> LENGTH: 27
<212> TYPE: DNA
<213> ORGANISM: Bacillus anthracis

<400> SEQUENCE: 7
gtgatttttc tgaatattaa gaaaaac                                         27

<210> SEQ ID NO 8
<211> LENGTH: 9
<212> TYPE: PRT
<213> ORGANISM: Bacillus anthracis

<400> SEQUENCE: 8

Met Ile Phe Leu Asn Ile Lys Lys Asn
1               5

<210> SEQ ID NO 9
<211> LENGTH: 300
<212> TYPE: DNA
<213> ORGANISM: Bacillus anthracis

<400> SEQUENCE: 9
acagaaaaag ttgcttttct caaatatgaa atattgcata taaaaatgaa ttgatgcaaa     60
tgtaaaagct tattataatg aaagcataaa tattcaacac atctttatac agcaaagagg    120
aggaagtaat atggaaatcg caatggcagt tttaaaattt ttaggtggag taattccttt    180
agttcaagaa cttttaaaag cgtttatgta aggttattcg ttagctatca tgtatccatc    240
attattatat cttactaaaa aagaacgggg tgatttttct gaatattaag aaaacacta    300
```

REGULATION OF GENE EXPRESSION BY THE *BACILLUS ANTHRACIS* ARP

CROSS-REFERENCE TO RELATED APPLICATIONS

This application claims benefit under 35 USC §119(e) to U.S. Provisional Patent Application 60/816,017, filed Jun. 23, 2006, and U.S. Provisional Patent Application 60/857,862, filed Nov. 10, 2006.

STATEMENT REGARDING FEDERALLY SPONSORED RESEARCH OR DEVELOPMENT

This invention was produced in part using funds from the Federal government under grant no. NIH U54 AIO57168. Accordingly, the Federal government has certain rights in this invention.

BACKGROUND OF THE INVENTION

1. Field of Invention

This invention relates to regulating Anthrolysin O expression in *Bacillus anthracis* and *Bacillus cereus* and *Bacillus thuringiensis*.

2. Description of Related Art

*Bacillus anthracis* is the causative agent of anthrax, an often fatal zoonosis. *B. anthracis* is a large, non-motile, Gram-positive rod shape bacteria. When *B. anthracis* encounter stress or nutrient limitation it produces spores. Spores are resistant to a wide range of physical and chemical agents and can survive in the soil for decades. The hardiness of the spores together with the ease of producing them make that *B. anthracis* was developed as a bio-weapon. The bioterror letter attacks of 2001 have stressed the need of a better understanding of the disease to prevent and cure possible future attacks.

For more than fifty years only two virulence factors have been known and intensely studied: the poly-D-glutamyl capsule which is encoded by virulence plasmid pX02, and. anthrax toxin, encoded by pXO1. Anthrax toxin is made of three peptides: lethal factor (LF), edema factor (EF) and protective antigen (PA). LF or EF were combined with PA to make two different A/B7 toxins. The seven PA subunits form a pore that transports the enzymatic toxin part (LF or EF) into the target cells. LF is zinc metalloprotease that cleaves the MAPK kinase, an important enzyme in intracellular signal transduction. EF is a calcium and calmodulin-dependent adenylate cyclase that increases the intracellular amount of cAMP thus disrupting the flow of ions and water and causing edema.

These virulence factors account for the some of the pathology, morbidity and mortality observed with *B. anthracis* and have been extensively studied. In addition to those well studied virulence factors, *B. anthracis* genome analysis has shown a whole array of other putative virulence factors: phospholipases, enterotoxins, hemolysins, and a cholesterol dependant cytolysin (CDC) (Read T D et al. The genome sequence of *Bacillus anthracis* Ames and comparison to closely related bacteria. Nature. 2003 May 1; 423(6935):81-6.). The roles of these virulence factors remain to be elucidated. Inventors have focused on the study *B. anthracis* cholesterol-dependent cytolysin (CDC) named anthrolysin O (ALO) (Shannon J G, Ross C L, Koehler T M, Rest R F. Characterization of anthrolysin O, the *Bacillus anthracis* cholesterol-dependent cytolysin. Infect Immun. 2003 June; 71(6):3183-9; Mosser E M, Rest R F. The *Bacillus anthracis* cholesterol-dependent cytolysin, Anthrolysin O, kills human neutrophils, monocytes and macrophages. BMC Microbiol. 2006 Jun. 21; 6:56; Park J M, Ng V H, Maeda S, Rest R F, Karin M. Anthrolysin O and other gram-positive cytolysins are toll-like receptor 4 agonists. J Exp Med. 2004 Dec. 20; 200(12): 1647-55, all of which are incorporated by reference herein in their entireties). ALO has been described in Patent Application Publication US2006/0089305A1 which is incorporated herein in its entirety. CDCs are a family of poreforming cytolysins that are proven virulence factors in more than 20 phylogenically unrelated Gram-positive pathogenic bacteria among which are *Listeria monocytogenes, Streptococcus pneumoniae, Streptococcus pyogenes*, and *Clostridium perfringens*. The formation of pores by most CDCs are dependent upon the presence of cholesterol in the membranes. CDCs are secreted as soluble monomeric proteins that bind to membranes and oligomerizes on the surface. The oligomers then insert into the membrane forming a pore. The CDC pore is made of 35 to 50 monomers and has a diameter of 25 to 30 nm.

*Bacillus cereus* and *Bacillus thuringiensis*, two species closely related to *B. anthracis* express CDCs, cereolysin O (CLO) and thuringiolysin O (TLO), respectively. In these organisms the expression of CDCs is controlled by the pleiotropic transcriptional activator PlcR. The activation of the PlcR regulon occurs at the onset of stationary phase by a quorum sensing mechanism and is triggered by a small peptide PapR (Ross C L, Koehler T M. plcR papR-independent expression of anthrolysin O by *Bacillus anthracis*. J. Bacteriol. 2006 November; 188(22):7823-9, incorporated by reference herein in its entirety). In *B. anthracis*, PlcR is inactive due to a nonsense mutation in the plcR gene. Therefore, it was believed that the PlcR regulon was silent in *B. anthracis* and, in particular, it was perceived that it produced no CDC and was therefore non-hemolytic. To the contrary, inventors have discovered contrary evidence that the *B. anthracis* CDC, ALO, is regulated by a mechanism different from *B. cereus* and *B. thuringiensis*.

All references cited herein are incorporated herein by reference in their entireties.

BRIEF SUMMARY OF THE INVENTION

In *Bacillus cereus* and *Bacillus thuringiensis* many virulence genes are regulated by the pleiotropic transcriptional activator PlcR. Among the genes regulated are cholesterol dependent cytolysins (CDCs). The CDC of *B. anthracis* (BA) is called Anthrolysin O (ALO). In BA, PlcR is truncated due to a mutation in the plcR gene. Thus, it is believed that the genes of the PlcR regulon, including alo, are not expressed. However, Shannon et al. demonstrated that ALO is expressed under certain growth conditions and that its expression is regulated by environmental signals. Defining the regulation of ALO expression is important as it will provide information on the role it plays during infection. Cloning the alo gene in a low copy number plasmid pUTE544 results in an appreciatively 1000-fold over-expression of ALO. We have found that upstream of the alo gene there is a 78 nt open reading frame. We propose that the peptide coded by this ORF is involved in alo regulation and we have named this peptide "ALO Regulating Peptide I" (ARP1). arp1 and alo are transcribed as a bicistronic operon. In spite of lacking a functional PlcR, we have demonstrated that the PlcR box located upstream of alo is involved in its regulation. The deletion or mutagenesis of the PlcR Box results in decreased expression of ALO. Our data show that BA regulates its CDC differently than *B.*

*cereus* and *B. thuringiensis*. BA regulates ALO expression using a newly identified regulator, ARP1, as well as the PlcR Box.

The invention provides an isolated nucleic acid sequence selected from the group consisting of SEQ ID NO: 1, SEQ ID NO: 3, fragments thereof, variants thereof, and mutants thereof. The invention provides an isolated nucleic acid sequence encoding a polypeptide selected from the group consisting of SEQ ID NO: 2, SEQ ID NO: 4, fragments thereof, mutants thereof, and variants thereof. The invention provides a recombinant DNA construct comprising a coding sequence encoding full length ARP1 or ARP2. The invention provides a recombinant DNA construct comprising a sequence encoding a protein selected from the group consisting of ARP1, ARP2, variants thereof, and mutants thereof. The invention provides a nucleic acid comprising a reporter gene operatively linked to a PlcR Box region of SEQ ID NO: 5. The invention further provides the nucleic acid, wherein the reporter gene is a luciferase gene. The invention further provides the nucleic acid, further comprising a polypeptide selected from the group consisting of SEQ ID NO: 2, SEQ ID NO: 4, fragments thereof, mutants thereof, and variants thereof. The invention further provides the nucleic acid, wherein the PlcR Box region is responsive to ARP1 and/or ARP2. The invention provides a host cell comprising a nucleic acid comprising a reporter gene operatively linked to a PlcR Box region of SEQ ID NO: 5, wherein the PlcR Box region is responsive to ARP1 and/or ARP2. The invention further provides a host cell, wherein the host cell is a member selected from the group consisting of eukaryotic cells and prokaryotic cells. The invention provides a cell line stably transfected with the nucleic acid of claim 7, wherein the PlcR Box region is responsive to ARP1 and/or ARP2.

The invention provides a substantially purified polypeptide selected from the group consisting of SEQ ID NO: 2, SEQ ID NO: 4, fragments thereof, mutants thereof, and variants thereof. The invention further provides the substantially purified polypeptide, having antimicrobial activity.

The invention provides an antibody having the ability to specifically bind to a substantially purified polypeptide selected from the group consisting of SEQ ID NO: 2, SEQ ID NO: 4, fragments thereof, mutants thereof, and variants thereof, further wherein the antibody is of polyclonal origin, further wherein the antibody is of monoclonal origin. The invention provides an isolated antibody, wherein said antibody selectively binds a) an ARP polypeptide with an amino acid sequence of SEQ ID NO: 2; b) an ARP polypeptide with an amino acid sequence of SEQ ID NO: 4; c) an ARP polypeptide that is encoded by a nucleic acid molecule that hybridizes to the nucleic acid sequence of SEQ ID NO: 1 under stringent conditions, comprising 50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; d) an ARP polypeptide that is encoded by a nucleic acid molecule that hybridizes to the nucleic acid sequence of SEQ ID NO: 2 under stringent conditions, comprising 50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; e) a fragment of said antibody, wherein said antibody and antibody fragment selectively bind to said ARP polypeptide and block the binding of ARP to PlcR. The invention provides an isolated antibody, wherein the antibody selectively binds to a polypeptide selected from the group consisting of SEQ ID NO: 2, SEQ ID NO: 4, fragments thereof, mutants thereof, and variants thereof, or a fragment of the antibody, wherein the antibody and antibody fragment selectively bind to the polypeptide and block the binding of the polypeptide to PlcR. The invention further provides an isolated antibody or fragment thereof, further defined as a scAb, Fab or SFv, further wherein, further defined as comprising an Fc domain of 1gA, 1gD, IgE, 1gG or 1gM, further wherein the antibody is a humanized antibody. The invention further provides an isolated antibody or fragment thereof, comprising an scFv fragment and antibody constant regions forming a monovalent antibody portion of at least 40 kDa.

The invention provides a recombinant *Bacillus* whose genome comprises a recombinant DNA construct comprising a coding sequence encoding a polypeptide selected from the group consisting of SEQ ID NO: 2, SEQ ID NO: 4, fragments thereof, mutants thereof, and variants thereof. The invention provides a recombinant *Bacillus* whose genome comprises a recombinant DNA construct comprising a coding sequence encoding a polypeptide selected from the group consisting of SEQ ID NO: 2, SEQ ID NO: 4, fragments thereof, mutants thereof, and variants thereof. The invention provides a recombinant bacteria whose genome comprises a recombinant DNA construct comprising a coding sequence encoding a polypeptide selected from the group consisting of SEQ ID NO: 2, SEQ ID NO: 4, fragments thereof, mutants thereof, and variants thereof. The invention provides a method for producing a recombinant *Bacillus* whose genome comprises a recombinant DNA construct a coding sequence encoding a polypeptide selected from the group consisting of SEQ ID NO: 2, SEQ ID NO: 4, fragments thereof, mutants thereof, and variants thereof under the control of a promoter. The invention provides an method for producing a recombinant *Bacillus* whose genome comprises a recombinant DNA construct comprising a coding sequence encoding a polypeptide selected from the group consisting of SEQ ID NO: 2, SEQ ID NO: 4, fragments thereof, mutants thereof, and variants thereof.

The invention provides a vaccine for the protection of humans against anthrax, comprising: a recombinant vector virus that expresses in vivo a heterologous nucleic acid sequence encoding a protein having an amino acid sequence selected from the group consisting of SEQ ID NO: 2, SEQ ID NO: 4, fragments thereof, and variants thereof, that specifically bind with antibody raised against said polypeptide; together with a pharmaceutically acceptable carrier. The invention provides an process for the protection of humans against anthrax comprising administering a vaccine according to the humans. The invention provides an vaccine for the protection of humans against anthrax, comprising: a vector virus that expresses in vivo a heterologous nucleic acid sequence selected from the group consisting of SEQ ID NO:1, SEQ ID NO:3, and fragments thereof, together with a pharmaceutically acceptable carrier. The invention provides an process for the protection of humans against anthrax, comprising administering a vaccine to the humans. The invention provides an method of treating or preventing Anthrax infection in a mammalian subject comprising administering to said subject a therapeutically effective amount of a vaccine composition.

The invention provides an method of identification of compounds that modulate PlcR Box activity comprising: (a) providing a reporter vector comprising a reporter gene and an PlcR Box region, wherein the PlcR Box region is responsive to ARP1 and/or ARP2; (b) providing a test agent; (c) providing ARP1 and/or ARP2; (d) combining the reporter vector, the test agent, and ARP1 and/or ARP2; (e) measuring reporter gene activity in the presence of test agent; (f) measuring reporter gene activity in a control sample; and (g) comparing reporter gene activity in the control sample compared to the test sample, to identify a compound which modulates PlcR Box activity. The invention further provides the method wherein the reporter vector comprising a reporter gene and the PlcR Box region responsive to ARP1 and/or ARP2 is in a stably transfected cell line. The invention provides a method of identifying a compound for the treatment of anthrax infection comprises determining the effect of the compound on ARP1 and/or ARP2-induced activation of the PlcR Box. The invention provides a method of identifying a potential therapeutic agent which inhibits ARP-induced activation of the PlcR Box comprising the steps of: (a) providing a cell comprising a reporter gene operatively linked to an PlcR Box region; (b) contacting the cell with a test agent in the presence of ARP1 and/or ARP2, wherein a decrement in the expression of the reporter gene in the presence of ARP1 and/or ARP2 and the test agent, as compared to the expression of the reporter gene in the presence of ARP1 and/or ARP2 and the absence of the test agent, indicates that the test agent is a potential therapeutic. The invention provides an method of identifying a potential therapeutic agent which inhibits ARP-induced activation of the PlcR Box comprising the steps of: (a) providing a cell comprising a reporter gene operatively linked to an PlcR Box region, and a vector comprising the gene encoding ARP1 and/or ARP2; (b) contacting said cell with a test agent under conditions wherein said cells express ARP1 and/or ARP2, wherein a decrement in the expression of the reporter gene as compared to a control indicates that the test agent is a potential Anthrax therapeutic. The invention further provides the method, wherein the cell is a member selected from the group consisting of eukaryotic cells, and prokaryotic cells, and further wherein the reporter gene is a luciferase gene.

The invention provides an method of treating Anthrax infection in a patient in need thereof by administration of an effective amount of a compound which modulates the activity of a member of the group selected from ARP1, ARP2, ALO expression or activity, PlcR activity, and combinations thereof. The invention provides an assay kit comprising a reporter vector comprising the PlcR Box, wherein the PlcR Box is responsive to ARP1 and/or ARP2.

BRIEF DESCRIPTION OF SEVERAL VIEWS OF THE DRAWINGS

The invention will be described in conjunction with the following drawings in which like reference numerals designate like elements and wherein:

Figure 1:
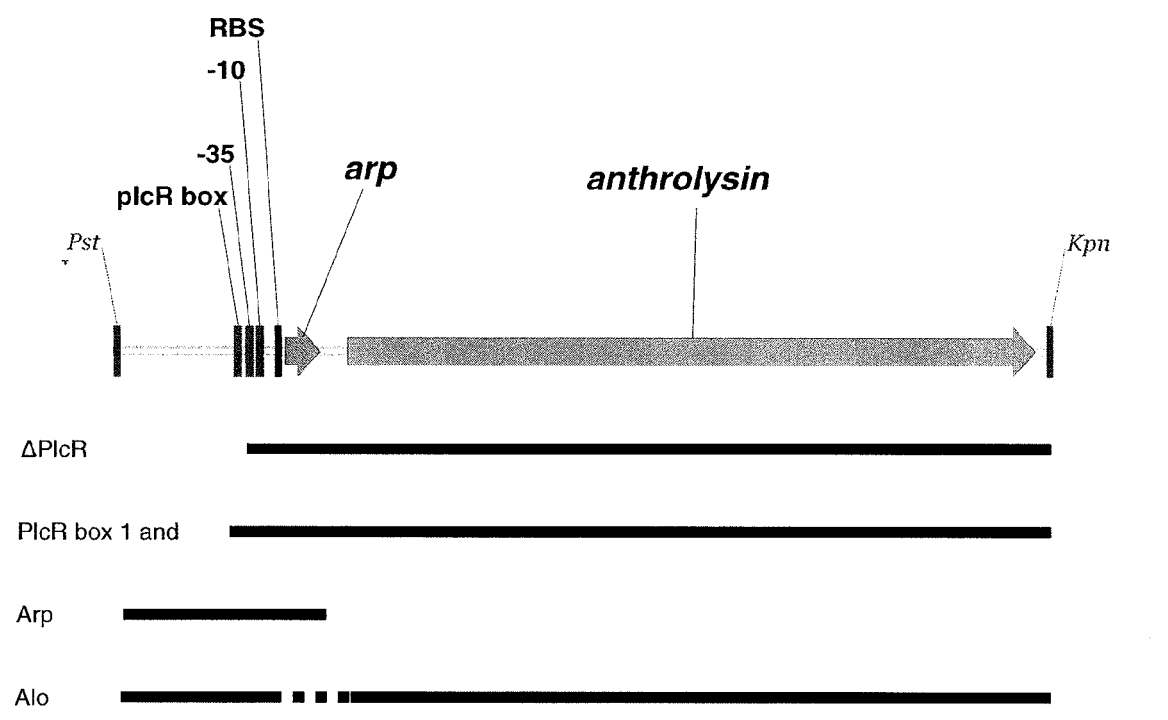

FIG. 1. Map of the arp1/alo operon. 5' Sequence of the arp1-alo operon including the promoter region, arp1 and the 5' sequence of alo. The PlcR Box, open reading frames with their translations below, and other regulatory sequences are highlighted. The dashed line in Alo ΔArp1 denotes a deletion. All mutants were constructed by PCR amplification and cloned in pUTE29, an *E. coli-B. anthracis* shuttle vector. All plasmids, except the one containing Arp1, which was cloned into 7702, were transformed by electroporation into the *B. anthracis* strain UT231, an ALO KO mutant of strain 7702.

FIG. 2. Sequence of the promoter region of the arp1/alo operon (SEQ ID NO: 9), arp1 nucleic acid (SEQ ID NO: 1) ARP amino acid sequence (SEQ ID NO: 2), alo nucleic acid sequence (SEQ ID NO: 7) ALO amino acid sequence (SEQ ID NO: 8) showing the precise positions of the deletions described in FIG. 1, above.

FIG. 3. ALO inhibits human neutrophil chemotaxis in a dose dependent manner, like LPS. Freshly isolated human peripheral neutrophils ($5\times10^6$/ml) were incubated for 20 min, or not, with LPS (lipopolysaccharide) or ALO (anthrolysin O) at the concentrations indicated, and then chemotaxis measured. Chemotaxis was through membranes towards interleukin-8 (IL-8), in a Neuroprobe chemotaxis chamber.

FIG. 4. ALO induces human neutrophil azurophil (primary) granule degranulation, unlike LPS. Freshly isolated human neutrophils were suspended in RPMI+10% serum and LPS (lipopolysaccharide) or ALO was added indicated concentrations (ng/ml). At 60 min, cell-free supernatant was obtained and myeloperoxidase (MPO) was measured as a direct indication of lysosome degranulation (or exocytosis). MPO was measured in a classic spectorphotometric assay.

FIG. 5. Mechanisms of ALO Modulation of Human Neutrophil Chemotaxis and Degranulation. ALO does different things to cells at different concentrations and under different conditions. At low concentrations (to the left of the figure) in the 10-250 ng/ml range, in the presence of serum, ALO stimulates through Toll Like Receptor 4 (TLR4) and perhaps other receptors, to stimulate intracellular signaling, leading to, amongst other things, release of proinflammatory cytokines, inhibition of chemotaxis, induction of neutrophil degranulation, and priming of the oxidative burst. At mid-range or high concentrations, in the absence of serum (i.e., in the absence of cholesterol), ALO kills by punching holes in the cell membrane.

FIG. 6. Arp1 is Required for Optimal ALO Expression. Strain 7702 is the 'parent' strain. Strain UT231 is the alo knockout. The plasmids are described at the bottom of the slide. pUTE544 has the complete arp1-alo operon. pDUM105 has just arp1, no alo. pDUM104 has no arp1, just alo. In the hemolysis assay, a red dot indicates no hemolysis, whereas red color and no red dot means total hemolysis. The assay consists of mixing overnight growth supernatants with human red blood cells, and waiting an hour. The 96 well plate has round bottom wells, so if there is no hemolysis, the red cells tumble to the bottom of the well and form a red dot. Bottom line: the parent strain transformed with arp1 [compare row 1 with row 3] produces about 500-fold more hemolysis (and thus 500-fold more ALO) than the parent strain. Similarly, the alo knockout transformed with the complete arp1-alo plasmid produces more than 1000-fold more ALO than the same strain transformed with the arp1 deficient plasmid [compare row 2 with row 4].

FIG. 7. Arp1 requires a PlcR Box for optimal activity. Plasmid pUTE544 contains the complete arp1-alo operon, with the complete promoter region. All pDUM plasmids shown in this figure are derivatives of pUTE544. Plasmids pDUM101, pDUM106 and pDUM107 each have a slightly different deletion of the PlcR Box. When transformed into the parent *B. anthracis* strain 7702, each of these plasmids leads to significantly less expression of alo than does the parent plasmid, pUTE544.

FIG. 8. Arp1 UP and DOWN Regulates Many proteins. SDS-PAGE Coomassie stained gels of whole bacteria comparing parent (7702) with the Arp1 overproducer. The bacteria were grown overnight in BHI broth, harvested, washed, boiled in prep buffer, and run on the gels.

FIG. 9. Number of differentially regulated genes (both up and down regulated) between the ARP over-producing strain 7702(pDUM105) and the parent strain 7702(pUTE29), as determined by microarray analysis. FIG. 10. Arp1 upregulates >33 genes involved in anaerobic growth. Genes identified from the microarray data in FIG. 9 were manually searched for those that might be involved in anaerobic metabolism.

FIG. 11. Germination-associated genes up regulated by over expression of arp1. Genes identified from the microarray data in FIG. 9 were manually searched for those that might be involved in germination.

FIG. 12. Genes upregulated by over expression of arp1 that contain a PlcR Box in their promoter. Genes identified from the microarray data in FIG. 9 were searched for those that had a consensus PlcR Box in their promoter.

FIG. 13. Phenotypes of an arp1 knock out strain of *B. anthracis*, strain BA558, compared to the parent strain, BA663. Compared to strain BA663, BA558 germinates more slowly, grows anaerobically more quickly, and regulates ALO expression in the presence of bicarbonate in a complex manner.

DETAILED DESCRIPTION OF THE INVENTION

The utility of the novel toxin regulatory gene and protein present in *Bacillus anthracis* is illustrated in Examples 1-4. It should also be recognized that the isolated novel toxin regulatory gene and protein of the present invention can be transferred into any microbial host and confer its insecticidal properties upon that host. Alternate hosts for the novel toxin regulatory gene and protein of the present invention can be selected as suitable for cloning purposes, for purposes of characterizing the form and function of the gene or encoded protein, for use as a fermentation host to increase production of the toxin protein, for purposes of delivering the toxin protein more effectively to the target insect pest, or introduction of the novel toxin regulatory gene into insect pathogens such as baculovirus to improve their effectiveness. It should be noted that the pharmaceutical compositions and antibodies may be utilized for human or veterinary applications or for agricultural applications. For example, the therapeutic composition may be administered to mammals such as, for example, humans, horses, cows, sheep, goats, cats, dogs, and pigs.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" refers to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of a mRNA. Examples of gene activation processes that increase transcription include, but are not limited to, those that facilitate formation of a transcription initiation complex, those that increase transcription initiation rate, those that increase transcription elongation rate, those that increase processivity of transcription and those that relieve transcriptional repression (by, for example, blocking the binding of a transcriptional repressor). Gene activation can constitute, for example, inhibition of repression as well as stimulation of expression above an existing level. Examples of gene activation processes which increase translation include those that increase translational initiation, those that increase translational elongation and those that increase mRNA stability. In general, gene activation comprises any detectable increase in the production of a gene product, in some instances an increase in production of a gene product by about 2-fold, in other instances from about 2- to about 5-fold or any integer therebetween, in still other instances between about 5- and about 10-fold or any integer therebetween, in yet other instances between about 10- and about 20-fold or any integer therebetween, sometimes between about 20- and about 50-fold or any integer therebetween, in other instances between about 50- and about 100-fold or any integer therebetween, and in yet other instances between 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, in some instances a decrease in production of a gene product by about 2-fold, in other instances from about 2- to about 5-fold or any integer therebetween, in yet other instances between about 5- and about 10-fold or any integer therebetween, in still other instances between about 10- and about 20-fold or any integer therebetween, sometimes between about 20- and about 50-fold or any integer therebetween, in other instances between about 50- and about 100-fold or any integer therebetween, in still other instances 100-fold or more. In yet other instances, gene repression results in complete inhibition of gene expression, such that no gene product is detectable.

"Modulation" refers to a change in the level or magnitude of an activity or process. The change can be either an increase or a decrease. For example, modulation of gene expression includes both gene activation and gene repression. Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, green fluorescent protein (see, e.g., Mistili & Spector, Nature Biotechnology 15:961-964 (1997))); changes in signal transduction, phosphorylation and dephosphorylation, receptor-ligand interactions, second messenger concentrations (e.g., cGMP, cAMP, IP3, and Ca2+), and cell growth. These assays can be in vitro, in vivo, and ex vivo. Such functional effects can be measured by any means known to those skilled in the art, e.g., measurement of RNA or protein levels, measurement of RNA stability, or identification of downstream or reporter gene expression, e.g., via chemiluminescence, fluorescence, colorimetric reactions, antibody binding, inducible markers, ligand binding assays, and the like.

It will be appreciated that a wide variety of host cells and vectors can be used for the instant invention. The term "host cell" refers to one or more cells into which a recombinant DNA molecule is introduced. A "vector" is a replicon, such as a plasmid, phage, or cosmid, to which another DNA segment may be attached so as to bring about the replication of the attached segment. A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, IRES ("internal ribosomal entry site") and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence. A control element, such as a promoter, "directs the transcription" of a coding sequence in a cell when RNA polymerase will bind the promoter and transcribe the coding sequence into mRNA, which is then translated into the polypeptide encoded by the coding sequence. Operably linked may also refer to an arrangement of two or more genes encoded on the same transcript. This arrangement results in the co-transcription of the genes, i.e., both genes are transcribed together since they are present on the same transcript. This operably linked arrangement of genes can be found in a naturally occurring DNA or constructed by genetic engineering. Further, according to this operable linkage, the genes can be translated as a polyprotein, i.e., translated as a fused polypeptide such that the resultant proteins are interlinked by a peptide bond from a single initiation event, or the genes can be translated separately from independent translation initiation signals, such as an IRES, which directs translation initiation of internally-situated open reading frames (i.e., protein-coding regions of a transcript.

ARP Nucleic Acids

One aspect of the present invention is the polynucleotide sequences essentially as set forth as SEQ ID NO: 1 and SEQ ID NO: 3, the complement of these sequences, the RNA versions of both DNA strands and the information otherwise contained within the linear sequence of these polynucleotide sequences and fragments thereof. The polynucleotide encoding ARP1 is exemplified by SEQ ID NO: 1, and the polynucleotide encoding ARP2 is exemplified by SEQ ID NO: 3. In the case of nucleic acid segments, sequences for use with the present invention are those that have greater than about 50 to 60% homology with any portion of the polynucleotide sequences described herein, sequences that have between about 61% and about 70%; sequences that have between about 71 and about 80%; or between about 81% and about 90%; or between 91% and about 99%; or which contain nucleotides that are identical, functionality equivalent, or functionally irrelevant, with respect to the nucleotides present in SEQ ID NO: 1 and SEQ ID NO: 3 are considered to be essentially similar. Also encompassed within the present invention are nucleic acids that encode polypeptides that are at least 40% identical or similar to the amino acid sequences shown in SEQ ID NO: 2 and SEQ ID NO: 4.

The invention also encompasses other nucleic acids or nucleic acid like molecules that are sufficient in any regard to mimic, substitute for, or interfere with the ARP polynucleotide sequences, as exemplified by SEQ ID NO: 1 and SEQ ID NO: 3, or fragments thereof. It will also be understood that the nucleic acid and amino acid sequences may include additional residues, such as additional 5'- or 3'-sequences, and yet still be essentially as set forth in one of the sequences disclosed herein, so long as the sequence meets the criteria set forth, including the maintenance of functionality, or for the purpose of engineering altered functionality with respect to ARP.

Included within the invention are DNA or RNA segments including oligonucleotides, polynucleotides and fragments thereof, including DNA or RNA or nucleic acid-like sequences of genomic or synthetic origin, single or double stranded. The invention includes nucleic acid molecules, or nucleic acid-like molecules that are able to hybridize to the sequences in SEQ ID NO: 1 and SEQ ID NO: 3, under stringent or under permissive hybridization conditions, or to the complement of said sequences.

The invention also includes oligonucleotide, or oligonucleotide-like sequences such as phosphorthioate, or peptide nucleic acid sequences, that possess sufficient similarity with the sequences disclosed herein such that they are able to stably hybridize to the disclosed sequences, or their complements. Such sequences may be intended as antisense regulators of gene expression, or for the selective amplification or extension of adjoining sequences, for instance by PCR using a given annealing temperature, as would be determined by someone skilled in the art.

In addition to the sequences disclosed here, related sequences in other organisms, or homologs, will be readily identified by hybridization using the present sequences. This will facilitate the development of animal models for understanding disorders related to the overexpression, underexpression, or expression of forms with altered functionality, with respect to ARP sequences as exemplified by SEQ ID NO: 1 and SEQ ID NO: 3, and similar sequences. Thus, related genes, and related mRNA transcripts, can be identified by one skilled in the art. The invention thus encompasses methods for the use of the disclosed sequences in various screening procedures aimed at isolating such species. For instance, colony or plaque hybridization techniques can be performed using radiolabeled sequences as a probe to detect complementary sequences in genomic and cDNA libraries.

Hybridization conditions with respect to temperature, formamide and salt concentrations, in such studies are chosen by one skilled in the art and vary with respect to the organism from which sequences are being isolated, and the sequence similarity, or lack thereof, that is expected based on evolutionary distances. Similar techniques will apply to the isolation of the genomic sequences that encode ARP, as well as those that encode related genes from organisms other than humans. Reference is particularly made to flanking regions, including upstream sequences that encode the core promoter and regulatory regions, as well as downstream regions, introns and intron/exon boundaries. Similar techniques will also apply to the identification of mutant alleles, polymorphisms, deletions, insertions, and so forth, in genomic and cDNA sequences. These may occur within the ARP sequences themselves, or may occur in regulatory regions, introns, intron/exon boundaries, or may reflect various insertions, partial or whole gene deletions, or substitutions, any of which may affect biological activity of a gene and gene product. In the case of humans, the identification of interindividual genomic differences in the ARP genes will be useful in diagnostic determinations.

Whole or partial sequences referred to above may also be identified and isolated using techniques that involve annealing of short oligonucleotides to complementary sequences, such as those as might be present in the genomic DNA of a particular organism, or in genomic or cDNA, including expression cDNA, libraries. Thus, PCR is used to obtain DNA sequences homologous to, and which lie between, two primers, usually between 15 to 30 nucleotides which have annealing temperatures typically between 60-80 degrees Celsius may be substantially purified. The choice of primer sequences, annealing conditions (temperature), number of amplification cycles, choice of polymerase, and so forth would be within the knowledge of one skilled in the art. Amplification assays will be generally applicable to the identification of sequences homologous to ARP, to the identification of flanking genomic or cDNA sequences, to the identification of mutated alleles, and so forth, in a manner that lends itself to rapid diagnostics.

Variations in PCR technology are also relevant, such as reverse transcriptase mediated PCR, in which mRNA or total RNA is reverse transcribed typically with an oligo dT or gene specific primer prior to PCR amplification. Techniques are also available which utilize only one gene-specific primer, together with a linker or adapter primer as may be present in a vector or attached to the ends of the DNAs to be amplified. For instance, the Genome Walker (Clontech) technique allows the isolation of genomic DNA that flanks a given oligonucleotide primer. Techniques are also available in which altered oligonucleotides are employed to generate specific mutations, deletions, insertions, or fusions in the disclosed sequences, or fragments thereof, for instance site directed mutagenesis.

Naturally, it will be understood that this invention is not limited to the particular nucleic acid sequences presented herein. Recombinant vectors, including for example plasmids, phage, viruses, and other sequences, and isolated DNA or RNA segments may therefore variously include the ARP gene sequences or their complements, and coding regions, as well as those that may bear selected alterations or modifications that nevertheless include ARP segments or may encode biologically or experimentally relevant amino acid sequences. Such sequences may be created by the application of recombinant DNA technology, where changes are engineered based on the consideration of the nucleotides or amino acids being exchanged, deleted, inserted, fused, or otherwise modified.

Likewise, the current invention encompasses sequences that may be naturally present as extensions of, or insertions within, the sequences disclosed herein, including alternative or longer 5' or 3' mRNA sequences, or intronic and promoter genomic sequences, or allelic or polymorphic versions of a gene. Similarly, natural, artificial, or synthetic fusions of ARP, and fragments thereof, with unrelated nucleic acids or amino acids such as those that encode epitope tags, binding proteins, marker proteins, and other amino acid sequences are included.

ARP Proteins and Polypeptides

One aspect of the invention is the protein, polypeptide, oligopeptide, or amino acid sequences or fragments thereof, of ARP, essentially as set forth in SEQ ID NO: 2 and SEQ ID NO: 4. The ARP1 polypeptide is exemplified by SEQ ID NO: 2, and the ARP2 polypeptide is exemplified by SEQ ID NO: 4. Sequences that have greater than about 40-50% homology with any portion of the amino acid sequences described herein, sequences that have between about 51% and about 60%; sequences that have between about 61% and about 70% sequences that have between about 70 and about 80%; or between about 81% and about 90%; or between 91% and about 99%; or those that contain amino acids that are identical, functionally equivalent, or functionally irrelevant, for instance those specified by conservative, evolutionarily conserved, and degenerate substitutions, with respect to the amino acid sequences presented in SEQ ID NO: 2 and SEQ ID NO: 4 are included. Functions of the ARP polypeptides of the instant invention include but are not limited to binding of PlcR, and modulation of expression of ALO. The invention thus applies to ARP polypeptide sequences, or fragments thereof, and nucleic acids which encode such polypeptides, such as those of other species. Reference is particularly, but not exclusively, made to the conserved regions of ARP, in contrast to similarity throughout the entire length. The invention thus encompasses amino acid sequences, or amino acid-like molecules, that are sufficient in any regard to mimic, substitute for, or interfere with the ARP amino acid sequences, or fragments thereof.

The invention encompasses ARP amino acid sequences that have been altered in any form, either through the use of recombinant engineering, or through post-translational or chemical modifications, including those that may be produced by natural, biological, artificial, or chemical methods. Naturally, it will be understood that this invention is not limited to the particular amino acid sequences presented herein. Altered amino acid sequences include those which have been created by the application of recombinant technology such that specific residues, regions, or domains have been altered, and which may be functionally identical, or which may possess unique biological or experimental properties with regards to function or interactions with natural and artificial ligands.

For instance such modifications may confer longer or shorter half-life, reduced or increased sensitivity to ligands that modify function, ability to detect or purify polypeptides, solubility, and so forth. Alternatively, such sequences may be shorter oligopeptides that possess an antigenic determinant, or property that interferes, or competes, with the function of a larger polypeptide, and those that affect interactions between ARP and PlcR, other nucleic acid regions, and other proteins. Such sequences may be created by the application of the nucleotides or amino acids being exchanged, deleted, inserted, fused, or otherwise modified. Likewise, the current invention within, the sequences that may be naturally present as extensions of, or insertions within, the sequences disclosed herein, including alternative or longer N- and C-terminal sequences, or alternatively spliced protein isoforms.

Production and purification of polypeptides may be achieved in any of a variety of expression systems known to those skilled in the art, including recombinant DNA techniques, genetic recombination, and chemical synthesis. For instance, expression in prokaryotic cells may be achieved by placing protein coding nucleic sequences downstream of a promoter, such as T7, T3, lacI, lacZ, trp, or other cellular, viral, or artificially modified promoters including those that may be inducible by IPTG, tetracycline, maltose, and so forth. Such promoters are often provided for in commercially available recombinant DNA vectors such as pRSET ABC, pBluescript, pKK223-3, and others, or are easily constructed to achieve such a purpose, and often include the presence of multiple cloning sites (MCS) to facilitate typically contain efficient ribosome binding sites, and in some cases transcription termination signals.

Cells for the expression of such proteins are normally $E.$ $coli$, but could include $B.$ $subtilus,$ $B.$ $thuringiensis,$ $B.$ $anthracis,$ $Streptomyces$ or others prokaryotes. The incorporation of such recombinant DNA can be efficiently achieved by calcium chloride transformation, electroporation, and so forth. In the case of $E.$ $coli$, cells typically grow in LB media with an appropriate antibiotic selection, for instance ampicillin, chloramphenicol, tetracycline and so forth in order to retain the recombinant vector, although vectors which integrate into the cellular chromosome are also possible. The promoter of many recombinant expression vectors require induction by an inducer compound, for instance IPTG, to facilitate high levels of transcription initiation and subsequent protein production. In some instances, nucleic acid sequences within the coding region may be altered to suit the codon usage patterns of a gives model expression system or organism.

Peptides, oligopeptides and polypeptides may also be produced by chemical synthesis, for instance solid phase techniques, either manually or under automated control such as Applied Biosystems 431 peptide synthesizer (Perkin Elmer). After synthesis, such molecules are often further purified by preparative high performance liquid chromatography. Thus, the invention provides methods for the production of epitopes for antibody production, or the production of small molecules that enhance or interfere with a specific function or interaction of the ARP polypeptides.

Methods to produce and purify said polypeptides in eukaryotic systems are widely available and understood by those proficient in the art. Cells for such production are known to include yeast and other fingi, $Drosophila$ and Sf9 cells, cells of other higher eukaryotic organisms such as HeLa, COS, CHO and others, as well as plant cells. Similarly, expression could be achieved in prokaryotic or eukaryotic extracts that are able to translate RNAs into proteins, such as rabbit reticulocyte lysates.

Vectors

Vectors for expression in such systems are widely available both commercially or can be prepared. Such vectors typically are driven by promoters derived from cellular or viral genes, such as CMV, HSV, EBV, HSV, SV40, Adenovirus, LTRs, vaccinia, baculovirus polyhedrin promoter, CaMV, TMV, Rubisco, and so forth, and could obviously include the promoters for the ARP genes themselves. Such vectors are often designed be regulated by the presence of enhancer or other regulatory element sequences. Introduction of such vectors into cells is often achieved by calcium phosphate or DEAE dextran technologies, liposome mediated techniques, electroporation, or viral mediated infection. Maintenance of such vectors may be achieved by selectable marker such as that conferred by HSV thymidine kinase, HGPRTase, herbicide resistance, visible markers, and so forth.

Selection of an appropriate methodology would be within the scope of those skilled in such methodologies, using the current invention, and would include any combination of host cell and vector which can achieve desired production goals. For instance, the ability of a host cell to drive efficient fulllength polypeptide production, glycosylation, membrane anchoring, secretion, absence of contaminating mammalian proteins or infectious agents, proteolytic processing, lipid modification, phosphorylation and so forth may dictate the use of baculovirus/insect cell systems, mammalian cells systems, plant cell systems and so on. In the case of in vitro translation extracts, one embodiment is the coupled transcription and translation of a nonreplicable recombinant vector, where translation is often visualized by the incorporation of a radiolabeled amino acid. The system selected may further depend on the desirability of obtaining purified polypeptides for further characterization, on whether the intent is to evaluate the effect of the overexpressed proteins on cellular gene expression, in vivo or in vitro, to identify compounds that enhance or interfere with the function of the overexpressed polypeptides, or other purposes.

The invention also relates to cells which contain such recombinant constructs, where the host cell refers to mammalian, plant, yeast, insect, or other eukaryotic cells, or to prokaryotic, or archae, and vectors that are designed for a given host. Promoter-vector combinations could be chosen by a person skilled in these arts. In some cases, the desired outcome may not be protein, but RNA, and recombinant vectors would include those with inserts present in either forward or reverse orientations.

Many of the vectors and hosts have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP), and so forth which facilitate purification. Vectors may also be designed which contain elements for polyadenylation, splicing and termination, such that incorporation of naturally occurring genomic DNA sequences that contain introns and exons can be produced and processed, or such that unrelated introns and other regulatory signals require RNA processing prior to production of mature, translatable RNAs. Proteins produced in the systems described above could be subject to a variety of post-translational modifications, such as glycosylation, phosphorylation, nonspecific or specific proteolysis or processing.

Purification of ARP, or variants produced as described above can be achieved by any of several widely available methods. Cells may be subject to freeze-thaw cycles or sonication to achieve disruption, or may be fractionated into subcellular components prior to further purification. Purification may be achieved by one or more techniques such as precipitation with salts or organic solvents, ion exchange, hydrophobic interaction, HPLC and FPLC chromatograpic techniques. Affinity chromatographic techniques could include the use of polyclonal or monoclonal antibodies raised against the expressed polypeptide, or antibodies raised against or available for an epitopic tag such as HA or FLAG. Similarly, purification can be aided by affinity chromatography using fusions to the desired proteins such as GSH-affinity resin, maltose affinity resin, carbohydrate (lectin) affinity resin or, in a one embodiment, Ni-affinity resin, and so forth. In some instances purification is achieved in the presence of denaturing agents such as urea or guanidine, and subsequent dialysis techniques may be required to restore functionality, if desired.

Screening for Substances Affecting ALO and Other Protein Expression

The present invention provides the use of all or part of the nucleic acid sequence of the ARP1 and/or ARP2 in methods of screening for substances which modulate the activity of ARP1 and/or ARP2 and increase or decrease the level of, for example, ALO expression. The present invention provides the use of all or part of the nucleic acid sequence of the ARP1 and/or ARP2 in methods of screening for substances which modulate the activity of ARP1 and/or ARP2 and increase or decrease the level of the expression of other proteins. This invention also comprises compounds, compositions, and methods useful for modulating the expression and activity of other genes or proteins involved in pathways of ALO gene or promoter expression.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridize with the mRNA and which are labeled or may be used in a specific amplification reaction such as the polymerase chain reaction. Use of a reporter gene facilitates determination of promoter activity by reference to protein production.

Further provided by the present invention is a nucleic acid construct comprising an ARP1 and/or ARP2 region set out in SEQ ID NO: 1 or 3, or a fragment, mutant, allele, derivative or variant thereof able to promote transcription, operably linked to a heterologous gene, e.g. a coding sequence. Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a colored product. Many examples are known, including β-galactosidase and luciferase. β-galactosidase activity may be assayed by production of blue color on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labeled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

The level of expression in the presence of the test substance may be compared with the level of expression in the absence of the test substance. A difference in expression in the presence of the test substance indicates ability of the substance to modulate gene expression. An increase in expression of the heterologous gene compared with expression of another gene not linked to a promoter as disclosed herein indicates specificity of the substance for modulation of the promoter.

A promoter construct may be introduced into a cell line using any technique previously described to produce a stable cell line containing the reporter construct integrated into the genome. The cells may be grown and incubated with test agents for varying times. The cells may be grown in 96 well plates to facilitate the analysis of large numbers of compounds. The cells may then be washed and the reporter gene expression analyzed. For some reporters, such as luciferase the cells will be lysed then analyzed.

Following identification of a substance which modulates or affects promoter activity, the substance may be investigated further. Furthermore, it may be manufactured and/or used in preparation, i.e. manufacture or formulation, of a composition such as a medicament, pharmaceutical composition or drug. These may be administered to individuals in need of such treatment.

siNA

This invention comprises compounds, compositions, and methods useful for modulating ALO gene or promoter expression using short interfering nucleic acid (siNA) molecules. This invention also comprises compounds, compositions, and methods useful for modulating the expression and activity of other genes involved in pathways of, for example, ARP1, ARP2, ALO gene, or PlcR promoter expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression or activity of, for example, ARP1, ARP2, ALO gene, or PlcR promoter, or the activity or expression of other components of the ALO pathway.

A siNA of the invention can be unmodified or chemically-modified. A siNA of the instant invention can be chemically synthesized, expressed from a vector or enzymatically synthesized. The instant invention also features various chemically-modified synthetic short interfering nucleic acid (siNA) molecules capable of modulating ALO gene or PlcR promoter expression or activity in cells by RNA interference (RNAi). The use of chemically-modified siNA improves various properties of native siNA molecules through increased resistance to nuclease degradation in vivo and/or through improved cellular uptake. Further, contrary to earlier published studies, siNA having multiple chemical modifications retains its RNAi activity. The siNA molecules of the instant invention provide useful reagents and methods for a variety of therapeutic, diagnostic, target validation, genomic discovery, genetic engineering, and pharmacogenomic applications.

In one embodiment, the invention features a double-stranded short interfering nucleic acid (siNA) molecule that modulates, for example, ARP1, ARP2, ALO gene, or PlcR promoter expression and/or activity, wherein said siNA molecule comprises about 19 to about 21 base pairs.

In one embodiment, the invention features a siNA molecule that modulates, for example, ARP1, ARP2, ALO gene, or PlcR promoter expression and/or activity, for example, wherein the ALO gene or promoter comprises ALO encoding sequence. In one embodiment, the invention features a siNA molecule that modulates expression of a ALO gene or PlcR promoter, for example, wherein the ALO gene or promoter comprises ALO non-coding sequence or regulatory elements involved in ALO gene or PlcR promoter expression.

In one embodiment, the invention features a siNA molecule having RNAi activity against, for example, ARP1, ARP2, or ALO RNA, wherein the siNA molecule comprises a sequence complementary to any RNA having ALO encoding sequence. In another embodiment, the invention features a siNA molecule having RNAi activity against ARP1, ARP2, or ALO RNA, wherein the siNA molecule comprises a sequence complementary to an RNA having other ARP1, ARP2, or ALO encoding sequence, for example other mutant ARP1, ARP2, or ALO gene or promoters.

In one embodiment of the invention a siNA molecule comprises an antisense strand comprising a nucleotide sequence that is complementary to a nucleotide sequence or a portion thereof encoding, for example, an ARP1, ARP2, or ALO protein. The siNA further comprises a sense strand, wherein said sense strand comprises a nucleotide sequence of an ARP1, ARP2, or ALO gene or PlcR promoter or a portion thereof.

In another embodiment, a siNA molecule comprises an antisense region comprising a nucleotide sequence that is complementary to a nucleotide sequence encoding an ARP1, ARP2, or ALO protein or a portion thereof. The siNA molecule further comprises a sense region, wherein said sense region comprises a nucleotide sequence of an ARP1, ARP2, or ALO gene or PlcR promoter or a portion thereof.

In one embodiment, a siNA molecule of the invention has RNAi activity that modulates expression of RNA encoded by, for example, an ARP1, ARP2, or ALO gene. Because ARP1, ARP2, or ALO gene can share some degree of sequence homology with each other, siNA molecules can be designed to target a class of ARP1, ARP2, or ALO gene or alternately specific ARP1, ARP2, or ALO gene (e.g., polymorphic variants) by selecting sequences that are either shared amongst different ALO targets or alternatively that are unique for a specific ARP1, ARP2, or ALO target. Therefore, in one embodiment, the siNA molecule can be designed to target conserved regions of, for example, ARP1, ARP2, or ALO RNA sequences having homology among several ALO gene or promoter variants so as to target a class of ARP1, ARP2, or ALO gene with one siNA molecule. Accordingly, in one embodiment, the siNA molecule of the invention modulates the expression of, for example, one or both ARP1, ARP2, or ALO alleles in a subject. In another embodiment, the siNA molecule can be designed to target a sequence that is unique to a specific ARP1, ARP2, or ALO RNA sequence (e.g., a single ARP1, ARP2, or ALO allele or ARP1, ARP2, or ALO SNP) due to the high degree of specificity that the siNA molecule requires to mediate RNAi activity.

In one embodiment, nucleic acid molecules of the invention that act as mediators of the RNA interference gene silencing response are double-stranded nucleic acid molecules. In another embodiment, the siNA molecules of the invention consist of duplexes containing about 19 base pairs between oligonucleotides comprising about 19 to about 25 (e.g., about 18, 19, 20, 21, 22, 23, 24, 25 or 26) nucleotides. In yet another embodiment, siNA molecules of the invention comprise duplexes with overhanging ends of about 1 to about 3 (e.g., about 1,2, or 3) nucleotides, for example, about 21-nucleotide duplexes with about 19 base pairs and 3'-terminal mononucleotide, dinucleotide, or trinucleotide overhangs.

In one embodiment, the invention features one or more chemically-modified siNA constructs having specificity, for example, for ALO expressing nucleic acid molecules, such as RNA encoding a ALO protein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy a basic residue incorporation. These chemical modifications, when used in various siNA constructs, are shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C.

Test Agents

Test agents that can be screened with methods of the present invention include, for example, polypeptides, β-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, small molecules, siNA, siRNA, dsRNA, dsDNA, anti-senseDNA, nucleic acids, antibodies, polyclonal antibodies, monoclonal antibodies, structural analogs or combinations thereof. Some test agents are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be natural occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides or proteins.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. In some methods, combinatorial libraries of small molecule test agents as described above can be readily employed to screen for small molecule modulators of Arp1 and/or ARP2. A number of assays are available for such screening.

Libraries of test agents to be screened with the claimed methods can also be generated based on structural studies of, for example, ARP1, ARP2, or ALO or its fragments. Such structural studies allow the identification of test agents that are more likely to bind to ARP1, ARP2, or ALO. The three-dimensional structure of for example, ARP1, ARP2, or ALO or its fragments (e.g., its catalytic domain) can be studied in a number of ways, e.g., crystal structure and molecular modeling. Methods of studying protein structures using x-ray crystallography are well known in the literature. See Physical Bio-chemistry, (85-86). Computer modeling of a target protein (e.g., ARP1, ARP2, or ALO) provides another means for designing test agents for screening modulators of the target protein. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR).

Modulators of the present invention also include antibodies that specifically bind to, for example, ARP1, ARP2, or ALO. Such antibodies can be monoclonal or polyclonal. Such antibodies can be generated using methods well known in the art. For example, the production of non-human monoclonal antibodies, e.g., murine or rat, can be accomplished by, for example, immunizing the animal with, for example, ARP1, ARP2, or ALO or its fragment. Such an immunogen can be obtained from a natural source, by peptides synthesis or by recombinant expression.

Humanized forms of mouse antibodies can be generated by linking the CDR regions of non-human antibodies to human constant regions by recombinant DNA techniques. e(90) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to, for example, ARP1, ARP2, or ALO.

Human antibodies against ARP1, ARP2, or ALO can also be produced from non-human transgenic mammals having transgenes encoding at least a segment of the human immunoglobulin locus and an inactivated endogenous immunoglobulin locus. See, e.g., Lonberg et al., WO93/12227; Kucherlapati, WO 91/10741. Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using ARP1, ARP2, or ALO or fragments thereof.

Reporter Vector

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®. 2.0 from INVITROGEN® and BACPACK®. BACULOVIRUS EXPRESSION SYSTEM FROM CLONTECH Other examples of expression systems include STRATAGENE®'s COMPLETE CONTROL®. Inducible Mammalian Expression System, which involves a synthetic ecdysone-inducible receptor, or its pET Expression System, an E. coli expression system. Another example of an inducible expression system is available from INVITROGEN® which carries the T-REX® (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Preferred vectors may also be of bacterial origin, which may comprise a promoter of a bacteriophage such as phage or T7 which is capable of functioning in the bacteria. In one of the most widely used expression systems, the nucleic acid encoding the ### may be transcribed from the vector by T7 RNA polymerase (Studier et al, Methods in Enzymol. 185: 60-89, 1990). In the *E. coli* BL21 (DE3) host strain, used in conjunction with pET vectors, the T7 RNA polymerase is produced from the 1-lysogen DE3 in the host bacterium, and its expression is under the control of the IPTG inducible lac Uv5 promoter. This system has been employed successfully for over-production of many proteins. Alternatively, the polymerase gene may be introduced on a lambda phage by infection with an int-phage such as the CE6 phage, which is commercially available (Novagen, Madison, USA). Other vectors include vectors containing the lambda PL promoter such as PLEX® (Invitrogen, NL), vectors containing the trc promoters such as pTrcH is Xpress® (Invitrogen), or pTrc99 (Pharmacia Biotech, SE), or vectors containing the tac promoter such as pKK223-3 (Pharmacia Biotech), or PMAL (New England Biolabs, Mass., USA).

It will be appreciated that host cells and vectors can readily be obtained from publicly-available depositories, such as GenBank at the National Center for Biotechnology Information (U.S.A) or through any commercial source, such as from Stratagene (La Jolla, Calif.), New England Biolabs (Beverly, Mass.), or BD Biosciences (Palo Alto, Calif.). One of ordinary skill in the art will further appreciate that combinations of vectors and host cells can be tested for stability prior to use. Such stability testing can be carried out, for example, by examining the integrity of a plasmid vector isolated from a culture over time using known methods such as, restriction enzyme analysis in combination with agarose gel electrophoresis.

One of skill in the art will understand that cloning also requires the step of transforming a host cell with a recombinant nucleic acid molecule. A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer. For example, bacterial host cells, such as *E. coli* HB101, can be transformed by electroporation using any commercially-available electroporation apparatus known in the art, such as a GenePulser apparatus (Bio-Rad, Hercules, Calif.). In one embodiment, mammalian cells, such as BHK-21 cells or Vero cells (ATCC CCL-81), are transformed with a recombinant plasmid containing a cloned cDNA by the method of "transfection." The term "transfection" refers to the transfer of genetic material into a eukaryotic cell, such as a mammalian cell, from the external environment of the cell.

One of skill in the art will appreciate the variety of methods of transfection that are available in the art. Such methods include the nucleic acid/CaPO4 co-precipitation method, the diethylaminoethyl (DEAE)-dextran method, the polybrene method, the cationic liposome method ("lipofection"), the electroporation method, the microinjection method, and the microparticle bombardment method. A description of transfection methods can be found in M. A. Aitken et al., Molecular Biomethods Handbook, Chapter 20, p. 235-250.

In accordance with the instant invention, the DNA encoding the siNA, can be engineered to contain one or more genetic markers. The term "genetic marker" in accordance with the instant invention refers to a variation in the sequence and/or structure of a first nucleic acid molecule that allows it to be distinguished over a second nucleic acid molecule. The "variation" can include, but is not limited to, a deletion or insertion of nucleotides, one or more single nucleotide changes, a chemical modification to one or more nucleotides, such as a methylation, or one or more eliminated and/or added restriction enzyme recognition sequences. The genetic marker can be introduced into a nucleic acid, including but not limited to a chromosome, genome, plasmid vector, bacteriophage vector, or DNA fragment, by a variety of molecular and/or genetic methods known to one of ordinary skill in the art, such as by PCR, chemical mutagenesis, site-specific mutagenesis, and restriction fragment deletion, insertion or substitution.

According to another embodiment of the instant invention, in vitro transcription is carried out on a recombinant plasmid carrying a cloned cDNA of the invention, under the control of an expressible promoter (i.e., a promoter which is effectively enabled or activated in vitro in the presence of corresponding transcription factors and RNA polymerase). The transcription process generates a fully-infectious mRNA transcript that can be used to transfect (i.e., infect) a cell host, such as BHK-21 (hamster kidney cells) or Vero cells. In one embodiment, the cDNA is operably linked with the bacteriophage transcriptional promoter, T7; to enable the in vitro transcription of the cDNA using bacteriophage T7 DNA-dependent RNA polymerase. One of ordinary skill in the art will appreciate that any suitable promoter, such as, for example, SP6, T3, any bacterial, viral, phage, or eukaryotic promoter, for controlling the transcription of, for example, the ARP1, ARP2, ALO gene, or fragment thereof, and for controlling the expression of a nucleotide sequence encoding a reporter is contemplated by the present invention. It will be appreciated that the promoter is typically selected from promoters which are functional in mammalian cells susceptible to infection by the ARP1, ARP2, ALO gene, or fragment thereof, encoding sequences of the invention, although prokaryotic or phage promoters and promoters functional in other eukaryotic cells may be used. The promoter is typically derived from promoter sequences of viral or eukaryotic genes. For example, it may be a promoter derived from the genome of a cell in which expression or transcription of, for example, the ARP1, ARP2, ALO gene, or fragment thereof, encoding sequence or construct is to occur.

With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). Tissue-specific or cell-specific promoters specific for lymphocytes, dendritic cells, skin, brain cells and epithelial cells, for example the CD2, CD11c, keratin 14, Wnt-1 and Rhodopsin promoters, respectively. Preferably the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter, the human cytomegalovirus (CMV) IE promoter, or SV40 promoter.

It may also be advantageous for the promoters to be inducible so that the levels of expression of, for example, the ARP1, ARP2, ALO gene, or fragment thereof encoding sequence can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above. It will be appreciated that the sources of promoter sequences, which typically can be retrieved using recombinant techniques from different cloning vectors and plasmids, etc., can be obtained from commercial sources, such as, NEW ENGLAND BIOLABS, INC. (MA), PROMEGA CORPORATION (WI), or BD BIOSCIENCES (CA), or from the laboratories of academic research groups upon request.

Any method of in vitro transcription known to one of ordinary skill in the art is contemplated by the instant invention. It will be understood that the method of in vitro transcription of a DNA sequence relies on the operable linkage to an appropriate promoter and that the cognate RNA polymerase is used to direct transcription of the DNA starting at the promoter sequence. It will be further appreciated that the RNA polymerase and promoter can be of bacterial, eukaryotic, or viral (including bacteriophage) origin. Bacteriophage-RNA polymerases are very robust, and the availability of purified recombinant proteins facilitates the generation of large quantities of RNA from cloned cDNA sequences. In contrast, eukaryotic in vitro transcription systems yield relatively small quantities of RNA. Bacteriophage-RNA polymerases, such as from bacteriophages SP6, T7, and T3, are especially suitable for the generation of RNA from DNA sequences cloned downstream of their specific promoters because, first, their promoters are small and easily incorporated into plasmid vectors and second, the polymerases are quite specific for their cognate promoters, which results in very little incorrect transcriptional initiation from DNA templates. Any suitable promoter, however, is contemplated by the instant invention, including, for example, bacterial, phage, viral, and eukaryotic promoters. Strong termination sequences are not available for these polymerases so that DNA templates can be linearized with a restriction enzyme 3' to the desired end of the RNA transcript and the polymerase is forced to stop at this point-a process referred to as "run-off" transcription. A full description of in vitro transcription can be found in M. A. Aitken et al., Molecular Biomethods Handbook, Chapter 26, p. 327-334 and Sambrook, J. and D. W. Russell, Molecular Cloning: A Laboratory Manual, Third Edition (2001).

Figure 3:
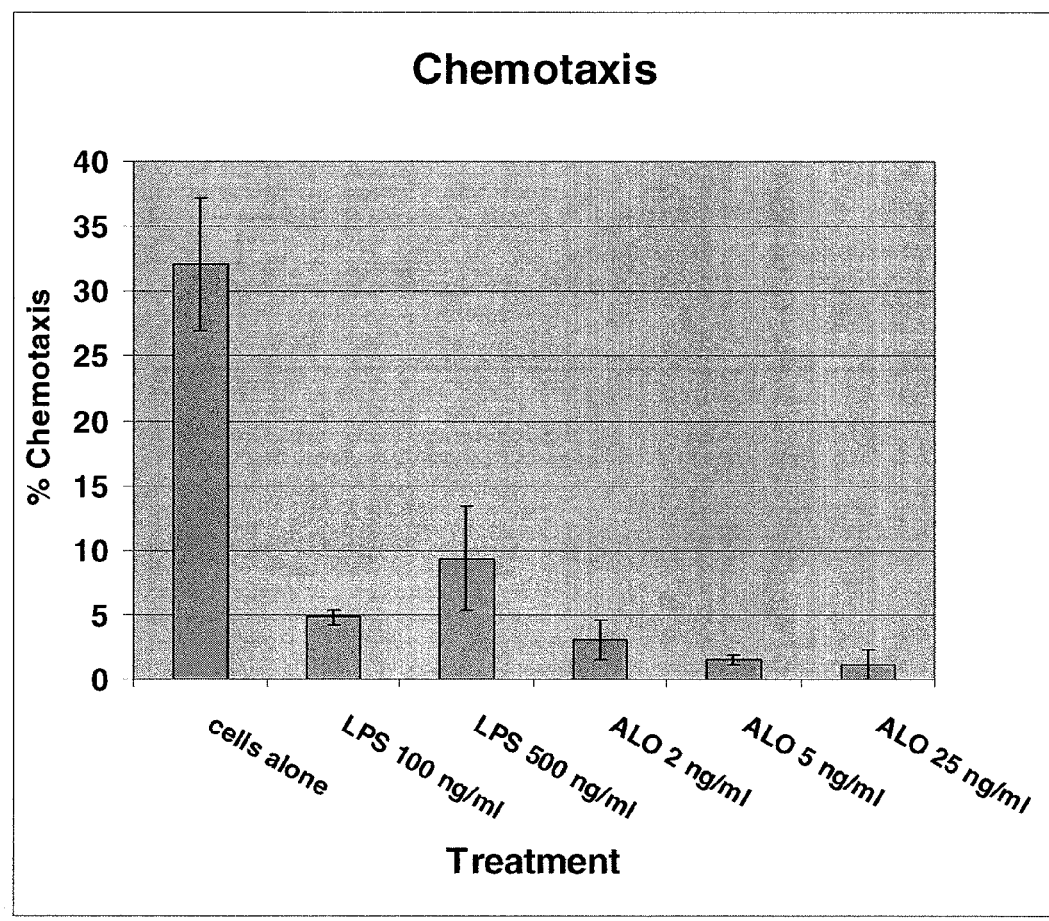

U.S. Pat. No. 6,143,502 (Grentzmann et al.) A dual luciferase reporter system for measuring recoding efficiencies in vivo or in vitro from a single construct has been designed (FIG. 3). The firefly luciferase gene (fluc) has been cloned behind the renilla luciferase gene (rluc) into an altered vector pRL-SV40 vector (Promega Corp., Madison, W is; catalog no. TB239). Expression features for initiation and termination of transcription and translation, as well as the nature of the two reporter genes (short enough to be efficiently synthesized in an in vitro translation system), allow application of the same reporter construct for in vivo and in vitro applications. Between the 5' reporter (rluc) and the 3' reporter (fluc) two alternative polylinkers have been inserted, yielding p2luc and p2luci. The p2luc polylinker has restriction sites for digestion with SalI, BamHI, and SacI, whereas the p2luci polylinker has restriction sites for digestion with SalI, ApaI, BglII, Eco47III, BamHI, SmaI, and SacI. The assay using these reporter plasmids combines rapidity of the reactions with very low background levels and provides a powerful assay. In vitro experiments can be performed in 96-well microtiter plates, and in vivo experiments can be performed in 6-well culture dishes. This makes the dual-luciferase assay suitable for high throughput screening approaches.

Target Antigens

A first embodiment of the present invention relates to an antibody that binds to an ARP1 protein. A typical amino acid sequence of ARP1 protein is shown in SEQ ID NO: 2. That is, an antibody according to the first embodiment of the present invention is preferably an antibody that specifically binds to the ARP1 polypeptide. ARP1 protein comprises SEQ ID NO: 2, and variants, fragments, muteins, etc., and those proteins derived from this protein. It is known that humans have a diversity of allele mutations and those proteins with one or more amino acids substituted, deleted, inserted, or added are also included in the ARP1 protein. However, it is not limited to these.

A typical amino acid sequence of ARP2 protein is shown in SEQ ID NO: 4. That is, an antibody according to the first embodiment of the present invention is preferably an antibody that specifically binds to the ARP2 polypeptide. ARP2 protein comprises an amino acid sequence as shown in SEQ ID NO: 4, and variants, fragments, muteins, etc., and those proteins derived from this protein. It is known that humans have a diversity of allele mutations and those proteins with one or more amino acids substituted, deleted, inserted, or added are also included in the ARP2 protein. However, it is not limited to these.

Fragments of the ARP1 or ARP2 protein may serve as the target antigen for the antibody binding. These antigen fragments may be about 6, 7, 8, 9, 10, 11, 12, 13, 14, 15, 16, 17, 18, 19, or 20 amino acids in length. The antigen fragments may by about 10, 20, 30, 40, 50, or 100 amino acids in length. The antibody of the present invention may be either a polyclonal antibody or a monoclonal antibody. To specifically detect a high molecular weight soluble ARP1 protein, it is desirable to use antibodies to certain limited epitopes and hence monoclonal antibodies are preferable. Molecule species are not particularly limited. Immunoglobulins of any class, subclass or isotype may be used.

Antibodies and Antibody Compositions

Additionally, the present invention includes a purified antibody produced in response to immunization with ARP1 and/or ARP2, as well as compositions comprising this purified antibody.

Antibodies refer to single chain, two-chain, and multi-chain proteins and glycoproteins belonging to the classes of polyclonal, monoclonal, chimeric, and hetero immunoglobulins; it also includes synthetic and genetically engineered variants of these immunoglobulins. "Antibody fragment" includes Fab, Fab', F(ab')2, and Fv fragments, as well as any portion of an antibody having specificity toward a desired target epitope or epitopes. A humanized antibody is an antibody derived from a non-human antibody, typically murine, that retains or substantially retains the antigen-binding properties of the parent antibody but which is less immunogenic in humans, U.S. Pat. No. 5,530,101, incorporated herein by reference in its entirety.

An antibody composition of the present invention is characterized as containing antibody molecules that immunoreact with ARP1 and/or ARP2, or a related polypeptide of this invention, but is substantially free of antibodies that immunoreact with any other related protein.

In accordance with the present invention, immunoglobulins specifically reactive with ARP2 related epitopes are provided. In accordance with the present invention, immunoglobulins specifically reactive with ARP1 related epitopes are provided.

In accordance with the present invention, humanized immunoglobulins specifically reactive with ARP2 related epitopes are provided. In accordance with the present invention, humanized immunoglobulins specifically reactive with ARP1 related epitopes are provided.

An antibody composition of the present invention is typically produced by immunizing a laboratory mammal with an inoculum of the present invention and to thereby induce in the mammal antibody molecules having the appropriate polypeptide immunospecificity. The antibody molecules are then collected from the mammal and isolated to the extent desired by well known techniques such as, for example, by immunoaffinity chromatography. The antibody composition so produced can be used in, inter alia, the diagnostic methods and systems of the present invention to detect ARP1 and/or ARP2 in a body sample.

The antibody compositions of this invention induced by a polypeptide of this invention, including an oligomeric polypeptide and a polypeptide polymer, can be described as being oligoclonal as compared to naturally occurring polyclonal antibodies since they are raised to an immunogen (the relatively small polypeptide) having relatively few epitopes as compared to the epitopes mimicked by an intact ARP1 and/or ARP2 molecule. Consequently, receptors of this invention bind to epitopes of the polypeptide, whereas naturally occurring antibodies raised to the whole ARP1 and/or ARP2 molecule bind to epitopes throughout the Arp1 and/or ARP2 molecule and are referred to as being polyclonal.

Monoclonal antibody compositions are also contemplated by the present invention. A monoclonal antibody composition contains, within detectable limits, only one species of antibody combining site capable of effectively binding ARP1 and/or ARP2. Thus, a monoclonal antibody composition of the present invention typically displays a single binding affinity for ARP1 and/or ARP2 even though it may contain antibodies capable of binding proteins other than ARP1 and/or ARP2.

Suitable antibodies in monoclonal form, typically whole antibodies, can also be prepared using hybridoma technology described by Niman et al., Proc. Natl. Sci., U.S.A., 80:4949-4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

Splenocytes are typically fused with myeloma cells using polyethylene glycol (PEG) 1500. Fused hybrids are selected by their sensitivity to HAT. Hybridomas secreting the receptor molecules of this invention are identified using the enzyme linked immunosorbent assay (ELISA).

A monoclonal antibody composition of the present invention can be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

The monoclonal antibody compositions produced by the above method can be used, for example, in diagnostic and therapeutic modalities wherein formation of aArp1 and/or ARP2-containing immunoreaction product is desired.

Diagnostic Systems and Kits

A diagnostic system in kit form of the present invention includes, in an amount sufficient for at least one assay, a polypeptide, antibody composition or monoclonal antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An examplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium or $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of ARP1 and/or ARP2 in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in preferred embodiments, a polypeptide, antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. In one embodiment a diagnostic system of the present invention is useful for assaying for the presence of Arp1 and/or ARP2. Such a system comprises, in kit form, a package containing an antibody to Arp1 and/or ARP2.

Host Cells

Host cells of the invention include, but are not limited to, bacterial cells, such as any Gram-positive, such as *Bacillus subtilis*, or Gram-negative bacterium, such as *Escherichia coli*, or any other suitable bacterial strain, fungal cells, such as the yeast *Saccharomyces cerevisiae*, animal cells, such as hamster, human, or monkey, plant cells, such as *Arabidopsis thaliana*, or insect cells, such as mosquito, or any other suitable cell. Host cells can be unicellular, or can be grown in tissue culture as liquid cultures, monolayers or the like. Host cells may also be derived directly or indirectly from tissues, such as liver, blood, or skin cells. Vectors can include plasmids, such as pBluescript SK, pBR322, and pACYC 184, cosmids, or virus/bacteriophage, such as pox virus vectors, baculovirus vectors, adenovirus vectors, and lambda, and artificial chromosomes, such as yeast artificial chromosomes (YAC), P1-derived artificial chromosomes (PACs) and bacterial artificial chromosomes (BACs), so long as they are compatible with the host cell, i.e., are stably maintained and replicated. Further, preferred prokaryotic vectors include plasmids such as those capable of replication in *E. coli*, for example, pBR322, ColE1, pSC101, pACYC 184, etc. (see Maniatis et al., Molecular Cloning: A Laboratory Manuel), *Bacillus* plasmids such as pC194, pC221, pT127, etc. (Gryczan, T., The Molecular Biology of the Bacilli, Academic Press, NY (1982), pp. 307-329); *Streptomyces* plasmids including pIJ101 (Kendall, K. J. et al., (1987) J. Bacteriol. 169:4177-4183); *Streptomyces* bacteriophages such as phiC31 (Chater, K. F. et al., in: Sixth International Symposium on Actinomycetal es Biology, Akademiai Kaido, Budapest, Hungary (1986), pp. 45-54), and *Pseudomonas* plasmids (John, J. F., et al. (1986) Rev. Infect. Dis. 8:693-704), and Izaki, K. (1978) Jpn. J. Bacteriol. 33:729-742). Preferred eukaryotic plasmids include BPV, vaccinia, SV40, 2-micron circle, etc., or their derivatives. Such plasmids are well known in the art (Botstein, D., et al. (1982) Miami Wint. Symp. 19:265-274; Broach, J. R., in: The Molecular Biology of the Yeast *Saccharomyces*: Life Cycle and Inheritance, Cold Spring Harbor Laboratory, Cold Spring Harbor, N.Y., pp. 445-470 (1981); Broach, J. R., (1982) Cell 28:203-204; Bollon, D. P., et al. (1980) J. Clin. Hematol. Oncol. 10:39-48; Maniatis, T., in: Cell Biology: A Comprehensive Treatise, Vol. 3: Gene Expression, Academic Press, N.Y., pp. 563-608 (1980)).

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE®. Competent Cells and SOLOPACK® Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12, etc. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Vaccine

Another aspect of the invention relates to a method for inducing an immunological response in an individual, particularly a mammal which comprises inoculating the individual with, for example, ARP1, ARP2, and/or ALO, or a fragment or variant thereof, adequate to produce antibody and/or T cell immune response to protect said individual from infection, particularly bacterial infection and most particularly *Streptococcus pneumoniae* infection. Also provided are methods whereby such immunological response slows bacterial replication. Yet another aspect of the invention relates to a method of inducing immunological response in an individual which comprises delivering to such individual a nucleic acid vector to direct expression of, for example, ARP1, ARP2, and/or ALO, or a fragment or a variant thereof, for expressing, for example, ARP1, ARP2, and/or ALO, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to, for example, a ARP1, ARP2, and/or ALO gene, or protein coded therefrom, wherein the composition comprises, for example, a recombinant ARP1, ARP2, and/or ALO gene or protein coded therefrom comprising DNA which codes for and expresses an antigen of said ARP or protein coded therefrom. The immunological response may be used therapeutically or prophylactically and may take the form of antibody immunity or cellular immunity such as that arising from CTL or CD4+T cells.

In an exemplary embodiment, an ARP1, ARP2, and/or ALO polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Streptococcus pneumoniae* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Streptococcus pneumoniae* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain ARP protein, it is to be understood that this covers fragments of the naturally occurring protein and similar proteins with additions, deletions or substitutions which do not substantially affect the immunogenic properties of the recombinant protein.

Microarrays

The method of the invention is particularly useful for the analysis of gene expression profiles. In some embodiments, a gene expression profile, such as a collection of transcription rates of a number of genes, is converted to a projected gene expression profile. The projected gene expression profile is a collection of expression values. The conversion is achieved, in some embodiments, by averaging the transcription rate of the genes. In some other embodiments, other linear projection processes may be used.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natd. Acad. Sci. 93:10614-10619; Baldeschweiler et al. (1995) PCT application WO95/251116; Shalon et al. (1995) PCT application WO95/35505; Heller et al. (1997) Proc. Natl. Acad. Sci. 94:2150-2155; and Heller et al. (1997)U.S. Pat. No. 5,605,662.) Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome DNA libraries.

The genes of the present invention are also useful in the design and preparation of microarrays. In particular, using the methods of the invention a skilled artisan can readily select and prepare probes for a microarray wherein the microarray contains specific individual probes for less than all the genes in the genome and less than all the genes in the genome. In such embodiments, the microarray contains one or two or more individual probes, each of which hybridizes to an expression product (e.g., mRNA, or cDNA or cRNA derived therefrom) for a desired number of genes. Thus, for example, changes in the expression of all or most of the genes in the entire genome of a cell or organism can thereby be monitored by use of a surrogate and on a single microarray by measuring expression of the group of genes that are representative of all or most of the genes of the genome. Such microarrays can be prepared using the selected probes and are therefore part of the present invention.

For example, in preferred embodiments, genes are identified, for a biological sample (e.g., a cell or organism) of interest. In general, the number of genes identified and for which probes appear in a microarray can be anywhere from 50 to 1,000. Preferably, however, the number of genes for which probes appear in a microarray will be fewer than 500, more preferably from 100 to 500, and still more preferably from 100 to 200. Representative genes are then selected from each genes identified, and probes are prepared that hybridize to the nucleotide sequence of each representative gene. Preferably, no more than ten representative genes are selected from each genes. More preferably, however, the number of representative genes selected from each genes for which probes appear on the microarray is no more than five, no more than four, no more than three or no more than two. In fact, most preferably only a single representative gene is selected from each genes for which one or more probes appear on the microarray. For at least one genes, and preferably for most or all of the genes, the number of representative genes for which probes appear on the microarray is less than the total number of genes in the genes. In certain preferred embodiments, at least one representative gene for which probes appear on the microarray is selected from all of the genes identified for the cell or organism. In other embodiments, the representative genes for which probes appear on the microarray are selected solely from genes that are associated with one or more particular biological states of interest. For example, in certain embodiments, the representative genes are selected from genes associated with a particular disease or disease state. In other embodiments, the representative genes are selected from genes whose change is expression is associated with a particular drug or with a particular therapy including, for example, genes whose change is expression is associated with drug or therapeutic efficacy or genes whose change in expression is associated with drug resistance or therapeutic failure. Thus, for example, in certain embodiments the total number of genes for which probes are present on a microarray is less than 1,000, less than 500, less than 200, less than 100, less than 50, less than 30, less than 20, or less than 10.

Treatment of Plants

The novel regulatory gene or recombinant forms thereof can be transformed into such alternate hosts using a variety of art recognized methods. One such preferred method is electroporation of microbial cells, as described, for example, by the method of Dower (U.S. Pat. No. 5,186,800). Another preferred method is that of Schurter et al. (Mol. Gen. Genet. 218:177-181 (1989)), which is also disclosed in U.S. Ser. No. 07/353,565 which is incorporated herein in its entirety.

It is envisioned that said alternate host would be applied to the environment or plants or animals for insect control. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

The present invention further provides an entomocidal composition comprising a recombinant *Bacillus* strain containing the novel regulatory gene in recombinant form, or a derivative or mutant thereof, together with an agricultural adjuvant such as a carder, diluent, surfactant or application-promoting adjuvant. The composition may also contain a further biologically active compound selected from fertilizers, micronutrient donors, plant growth preparations, herbicides, insecticides, fungicides, bactericides, nematicides and molluscicides and mixtures thereof. The composition may comprise from 0.1 to 99% by weight of the recombinant *Bacillus* strain containing the novel gene in recombinant form, or the derivative or mutant thereof, from 1 to 99.9% by weight of a solid or liquid adjuvant, and from 0 to 25% by weight of a surfactant. The recombinant *Bacillus* strain containing the novel gene in recombinant form, or the composition containing it, may be administered to the plants or crops to be protected together with certain other insecticides or chemicals (1993 Crop Protection Chemicals Reference, Chemical and Pharmaceutical Press, Canada) without loss of potency. It is compatible with most other commonly used agricultural spray materials but should not be used in extremely alkaline spray solutions. It may be administered as a dust, a suspension, a wettable powder or in any other material form suitable for agricultural application.

Target crops to be protected within the scope of the present invention comprise, e.g., the following species of plants: cereals (wheat, barley, rye, oats, rice, sorghum and related crops), beet (sugar beet and fodder beet), forage grasses (orchardgrass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), citrus fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

Entomocidal Compositions Comprising a Recombinant *Bacillus anthracis* Strain

The recombinant *Bacillus* strain containing the novel gene in recombinant form is normally applied in the form of entomocidal compositions and can be applied to the crop area or plant to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The formulations, i.e. the entomocidal compositions, preparations or mixtures containing the recombinant *Bacillus anthracis* strain containing the novel gene in recombinant form as an active ingredient or combinations thereof with other active ingredients, and, where appropriate, a solid or liquid adjuvant, are prepared in known manner, e.g., by homogeneously mixing and/or grinding the active ingredients with extenders, e.g., solvents, solid carriers, and in some cases surface-active compounds (surfactants).

Transgenic Plants Comprising the Novel Regulatory Gene or Protein

A host plant expressing the novel regulatory genes of the invention will have enhanced resistance to insect attack and will be thus better equipped to withstand crop losses associated with such attack.

The recombinant DNA molecules can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., Bio-Techniques 4:320-334 (1986)), electroporation (Riggs et al, Proc. Natl. Acad. Sci. USA 83:5602-5606 (1986), *Agrobacterium*-mediated transformation (Hinchee et at., Biotechnology 6:915-921 (1988)), direct gene transfer (Paszkowski et at., EMBO J. 3:2717-2722 (1984)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6:923-926 (1988)). Also see, Weissinger et al., Annual Rev. Genet. 22:421-477 (1988); Sanford et al., Particulate Science and Technology 5:27-37 91987)(onion); Christou et al., Plant Physiol. 87:671-674 (1988)(soybean); McCabe et al., Bio/Technology 6:923-926 (1988)(soybean); Datta et al., Bio/Technology 8:736-740 (1990)(rice); Klein et al., Proc. Natl. Acad. Sci. USA, 85:4305-4309 (1988) (maize); Klein et al., Bio/Technology 6:559-563 (1988) (maize); Klein et al., Plant Physiol. 91:440-444 (1988) (maize); Fromm et al., Bio/Technology 8:833-839 (1990); and Gordon-Kamm et al., Plant Cell 2:603-618 (1990) (maize); Svab et al. Proc. Natl. Acad. Sci. USA 87:8526-8530 (1990) (tobacco chloroplast); Koziel et al. (Biotechnology 11:194-200 (1993)) (maize); Shimamoto et al. Nature 338: 274-277 (1989)(rice); Christou et al. Biotechnology 9:957-962 (1991)(rice); European Patent Application EP 0 332 581 (orchardgrass and other Pooideae); Vasil et al. (Biotechnology 11:1553-1558 (1993) (wheat); Weeks et al. (Plant Physiol. 102:1077-1084 (1993) (wheat).

Pharmaceutical Compositions and Administration

Administration of therapeutically effective amounts of a compound which modulates, for example, ARP1, ARP2, and/or ALO expression or activity is by any of the routes normally used for introducing protein or encoding nucleic acids into ultimate contact with the tissue to be treated. The protein or encoding nucleic acids are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington's Pharmaceutical Sciences, 17th ed. 1985)).

The protein or encoding nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

In certain cases, alteration of a genomic sequence in a pluripotent cell (e.g., a hematopoietic stem cell) is desired. Methods for mobilization, enrichment and culture of hematopoietic stem cells are known in the art. See for example, U.S. Pat. Nos. 5,061,620; 5,681,559; 6,335,195; 6,645,489 and 6,667,064. Treated stem cells can be returned to a patient for treatment of various diseases including, but not limited to, SCID and sickle-cell anemia.

Dosages

For therapeutic applications, the dose administered to a patient, or to a cell which will be introduced into a patient, in the context of the present disclosure, should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy and Kd of the particular compound employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

In determining the effective amount of the compound which modulates, for example, ARP1, ARP2, and/or ALO expression or activity to be administered in the treatment or prophylaxis of disease, the physician evaluates circulating plasma levels of the compound which modulates, for example, ARP1, ARP2, and/or ALO expression or activity or nucleic acid encoding the compound which modulates ALO expression, potential compounds which modulates, for example, ARP1, ARP2, and/or ALO expression or activity toxicities, progression of the disease, and the production of antibodies. Administration can be accomplished via single or divided doses.

The invention will be illustrated in more detail with reference to the following Examples, but it should be understood that the present invention is not deemed to be limited thereto.

EXAMPLES

Example 1

Figure 4:
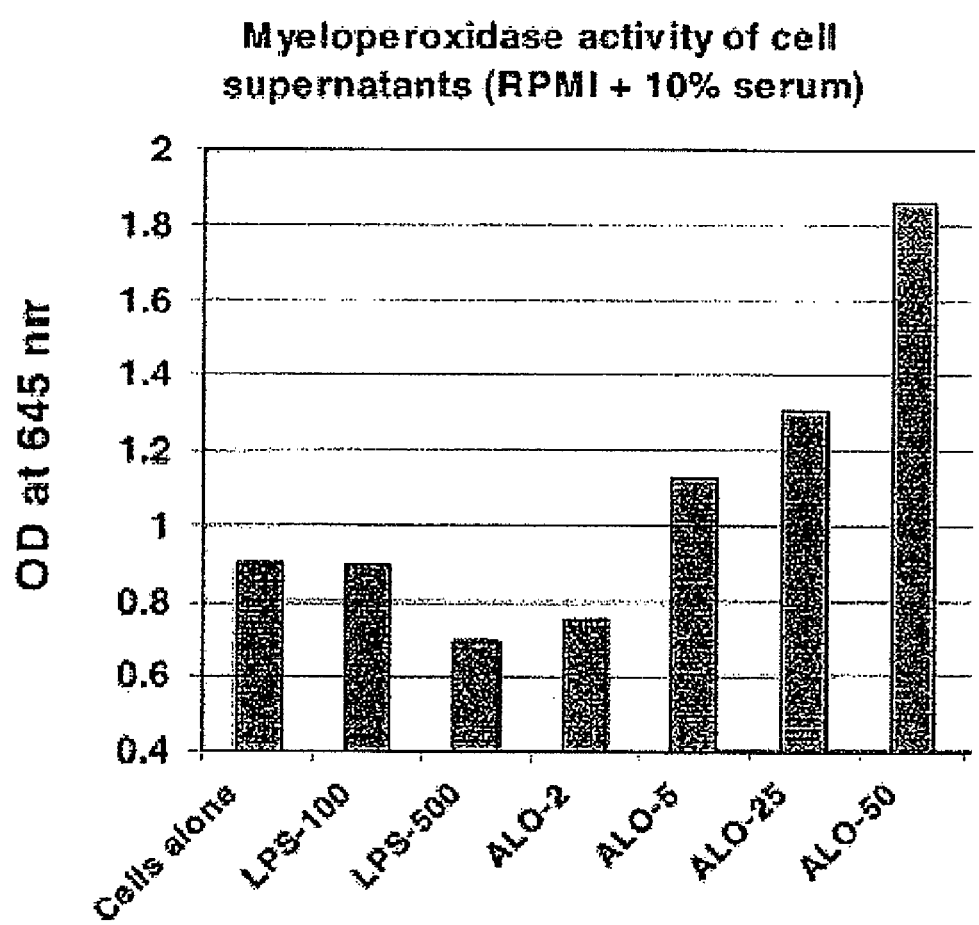

ALO induces human neutrophil azurophil (primary) granule degranulation, unlike LPS, referring to FIG. 4. Freshly isolated human neutrophils were suspended in RPMI+10% serum and LPS (lipopolysaccharide) or ALO was added at indicated concentrations (ng/ml). At 60 min, cell-free supernatant was obtained and myeloperoxidase (MPO) was measured as a direct indication of lysosome degranulation (or exocytosis). MPO was measured in a standard spectrophotometric assay.

Example 2

Figure 5:
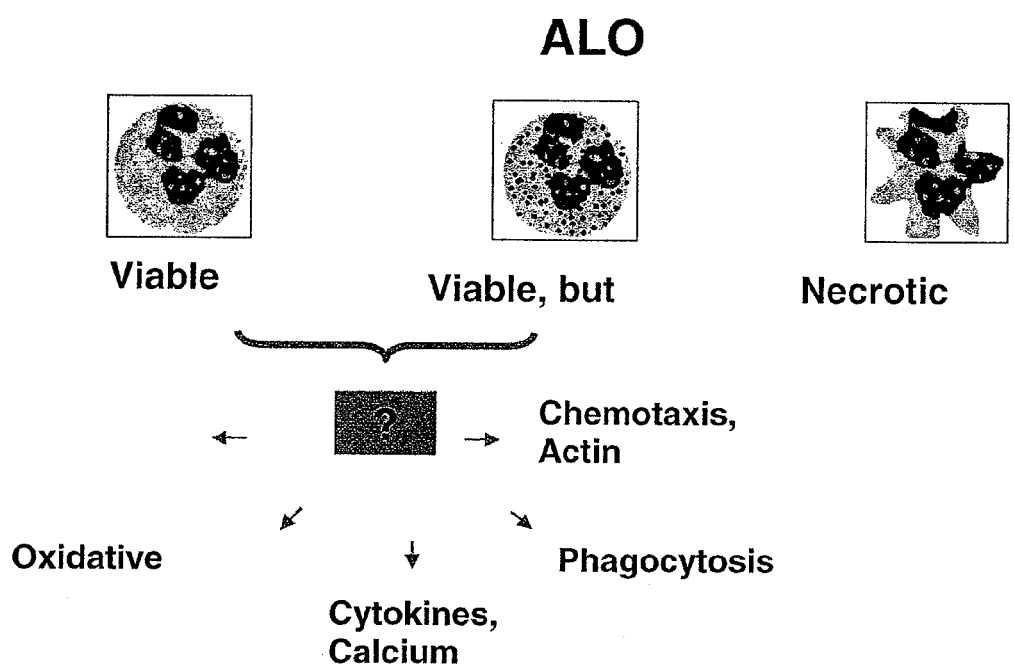

Mechanisms of ALO Modulation of Human Neutrophil Chemotaxis and Degranulation, referring to FIG. 5 ALO affects cells differently at different concentrations and under different conditions. At low concentrations (to the left of the figure) in the 10-250 ng/ml range, in the presence of serum, ALO stimulates through Toll Like Receptor 4 (TLR4) and perhaps other receptors, to stimulate intracellular signaling, leading to, amongst other things, release of proinflammatory cytokines, inhibition of chemotaxis, induction of neutrophil degranulation, and priming of the oxidative burst. At midrange or high concentrations, in the absence of serum (i.e., in the absence of cholesterol), ALO kills by punching holes in the cell membrane. This is a continuum, not a stepwise increasing situation.

Example 3

Figure 6:
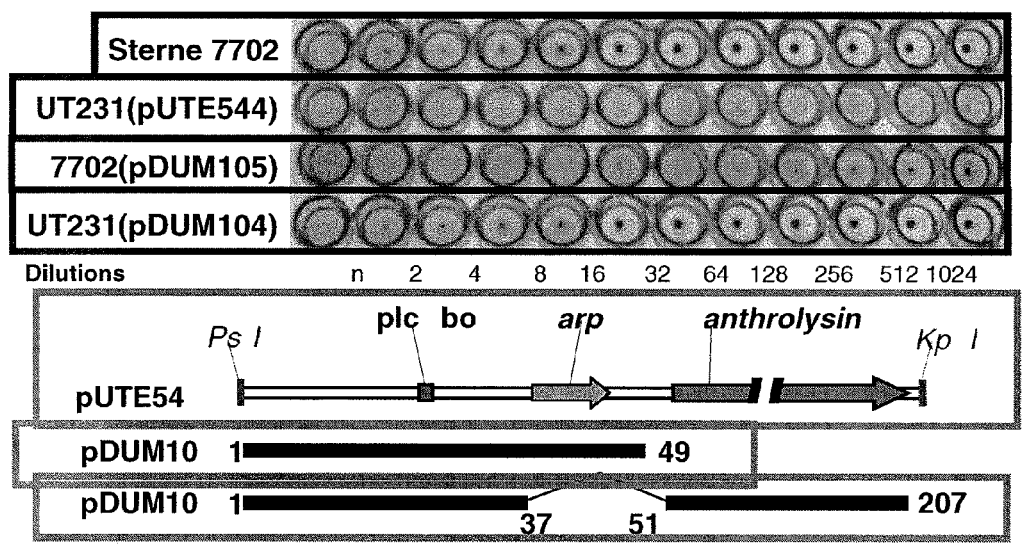
Figure 7:
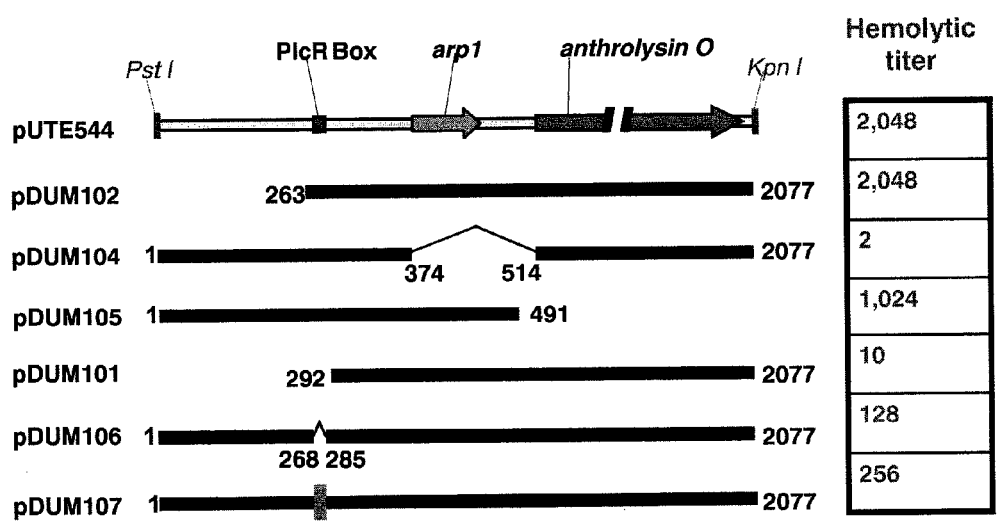

Arp1 is Required for Optimal ALO Expression. Strain 7702 is the 'parent' strain. Strain UT231 is an alo knockout, referring to FIG. 6. The plasmids are described at the bottom of the slide. pUTE544 contains the complete arp1-alo operon. pDUM105 has just arp1, no alo. pDUM104 has no arp1, just alo. In the hemolysis assay, a red dot indicates no hemolysis, whereas red color and no red dot means total hemolysis. In the assay overnight growth supernatants (free of bacteria) are mixed with human red blood cells and incubated for up to one hour. The 96 well plate has round bottom wells, so if there is no hemolysis, the red cells tumble to the bottom of the well and form a red dot. Observations and conclusions: the parent strain transformed with arp1 [compare row 1 with row 3] produces about 500-fold more hemolysis (and thus 500-fold more ALO) than the parent strain. Similarly, the alo knockout transformed with the complete arp1-alo plasmid produces more than 1000-fold more ALO than the same strain transformed with the arp1 deficient plasmid [compare row 2 with row 4].

Example 4

Figure 8:
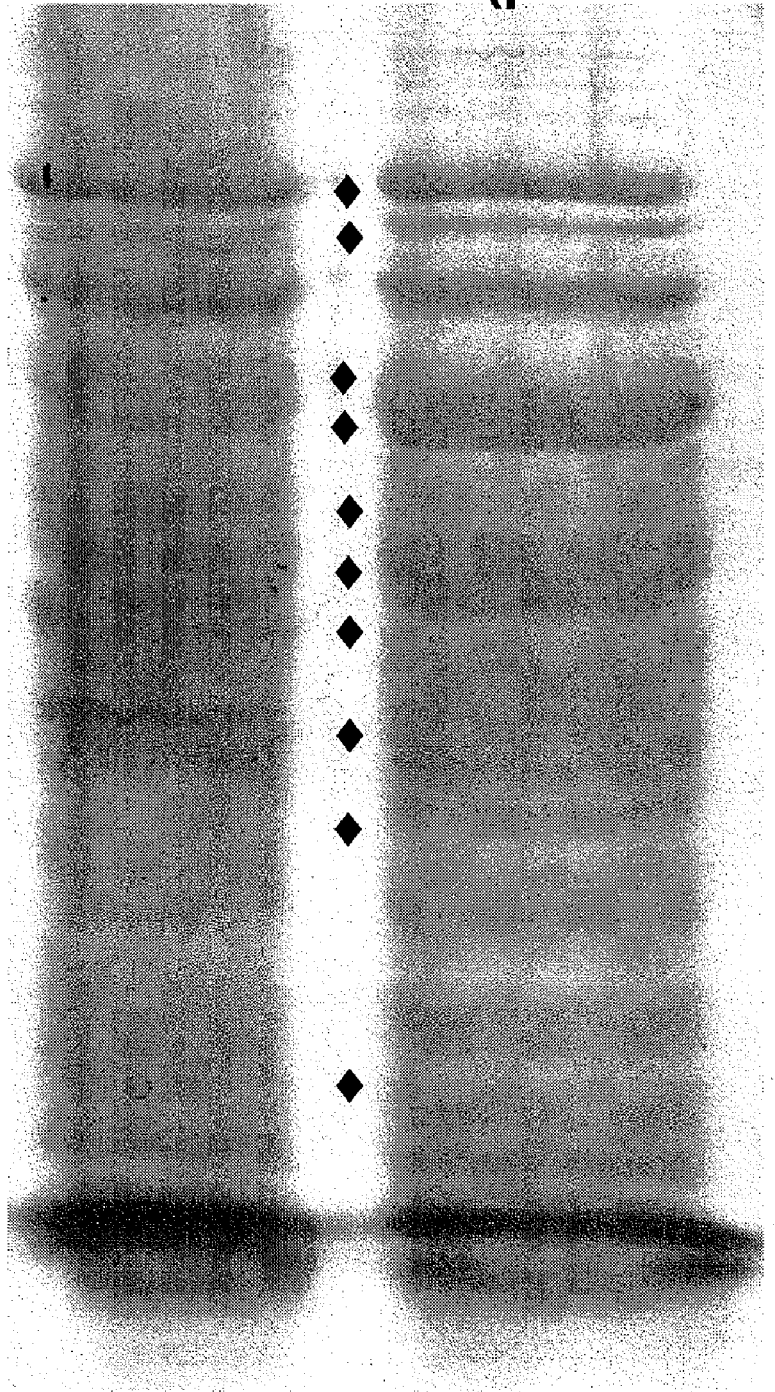

Arp1 modulates many proteins, referring to FIG. 8. SDS-PAGE Coomassie stained gels of whole bacteria comparing the parent strain (7702) with the Arp1 over expresser strain. Bacteria were grown overnight in BHI broth, harvested, washed, boiled in prep buffer, and run on SDS-PAGE gels.

Example 5

Genes upregulated by over expression of arp1 that contain a PlcR Box in their promoter, referring to FIG. 12. Genes identified from the microarray data in FIG. 11 were searched for those that had a consensus PlcR Box in their promoter.

While the invention has been described in detail and with reference to specific examples thereof, it will be apparent to one skilled in the art that various changes and modifications can be made therein without departing from the spirit and scope thereof.

---

What is claimed is:

1. An isolated nucleic acid sequence selected from the group consisting of SEQ ID NO: 1, SEQ ID NO: 3, and fragments thereof, wherein the nucleic acid encodes a peptide that binds PlcR Box.

2. An isolated nucleic acid sequence encoding a polypeptide selected from the group consisting of SEQ ID NO: 2, SEQ ID NO: 4, and fragments thereof, wherein the encoded polypeptide binds PlcR Box.

3. A nucleic acid comprising a reporter gene operatively linked to a PlcR Box region of SEQ ID NO: 5.

4. The nucleic acid of claim 3, wherein the reporter gene is a luciferase gene.

5. The nucleic acid of claim 3, further comprising a nucleic acid sequence encoding a polypeptide selected from the group consisting of SEQ ID NO: 2, SEQ ID NO: 4, and fragments thereof, wherein the PlcR Box region is responsive to ARP1 and/or ARP2, and further wherein the encoded polypeptide binds PlcR Box.

6. A host cell comprising the nucleic acid of claim 5, wherein the PlcR Box region is responsive to ARP1 and/or ARP2.

7. The host cell of claim 6, wherein the host cell is a member selected from the group consisting of eukaryotic cells and prokaryotic cells.

8. A cell line stably transfected with the nucleic acid of claim 5, wherein the PlcR Box region is responsive to ARP1 and/or ARP2.

9. A substantially purified polypeptide selected from the group consisting of SEQ ID NO: 2, SEQ ID NO: 4, and fragments thereof, wherein the polypeptide binds PlcR Box.

10. An isolated antibody or antibody fragment, wherein said antibody or antibody fragment selectively binds a polypeptide selected from the group consisting of:
   a) an ARP polypeptide with an amino acid sequence of SEQ ID NO:2;
   b) an ARP polypeptide with an amino acid sequence of SEQ ID NO:4;
   c) an ARP polypeptide that is encoded by a nucleic acid molecule that hybridizes to the nucleic acid sequence of SEQ ID NO:1 under stringent conditions, comprising 50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; and d) an ARP polypeptide that is encoded by a nucleic acid molecule that hybridizes to a nucleic acid sequence encoding SEQ ID NO:2 under stringent conditions, comprising 50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2× SSC and 0.1% SDS, wherein the antibody or antibody fragment selectively binds to the ARP polypeptide and blocks the binding of ARP to PlcR Box.

11. The antibody of claim 10, wherein said antibody is of polyclonal or monoclonal origin.

12. A recombinant cell whose genome comprises a recombinant DNA construct comprising a coding sequence encoding a polypeptide selected from the group consisting of SEQ ID NO: 2, SEQ ID NO: 4, and fragments thereof, wherein the polypeptide binds PlcR Box, and further wherein the recombinant cell is a member selected from the group consisting of eukaryotic cells and prokaryotic cells.

13. A method for producing the recombinant cell of claim 12, comprising:

providing a cell selected from the group consisting of eukaryotic cells and prokaryotic cells;

providing a recombinant DNA construct comprising a coding sequence encoding a polypeptide selected from the group consisting of SEQ ID NO: 2, SEQ ID NO: 4, and fragments thereof, wherein the polypeptide binds PlcR Box;

transfecting the cell with the recombinant DNA construct, thereby producing the recombinant cell.

14. A method of identifying a potential therapeutic agent for the treatment of anthrax infection which inhibits ARP-induced activation of the PlcR Box comprising the steps of:

(a) providing a reporter vector comprising a reporter gene and an PlcR Box region, wherein the PlcR Box region is responsive to ARP1 and/or ARP2;

(b) providing a test agent;

(c) providing ARP1 and/or ARP2;

(d) combining the reporter vector, the test agent, and ARP1 and/or ARP2;

(e) measuring reporter gene activity in the presence of test agent;

(f) measuring reporter gene activity in a control sample without test agent; and (g) comparing reporter gene activity in the control sample compared to the test sample, to identify a compound which modulates PlcR Box activity.

15. The method of claim 14, wherein the reporter vector comprising a reporter gene and the PlcR Box region responsive to ARP1 and/or ARP2 is in a stably transfected cell line.

16. The method of claim 15, wherein the cell line is a member selected from the group consisting of eukaryotic cells, and prokaryotic cells.

17. The method of claim 14, wherein the reporter gene is a luciferase gene.

18. A kit comprising a reporter vector comprising a PlcR Box, wherein the PlcR Box is responsive to ARP1 and/or ARP2.

* * * * *